United States Patent
He et al.

(10) Patent No.: US 12,062,429 B2
(45) Date of Patent: Aug. 13, 2024

(54) SALIENT VISUAL EXPLANATIONS OF FEATURE ASSESSMENTS BY MACHINE LEARNING MODELS

(71) Applicant: KONINKLIJKE PHILIPS N.V., Eindhoven (NL)

(72) Inventors: Ze He, Cambridge, MA (US); Binyam Gebrekidan Gebre, Rosmalen (NL); Christine Menking Swisher, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 595 days.

(21) Appl. No.: 17/270,150

(22) PCT Filed: Aug. 21, 2019

(86) PCT No.: PCT/EP2019/072323
§ 371 (c)(1),
(2) Date: Feb. 22, 2021

(87) PCT Pub. No.: WO2020/038974
PCT Pub. Date: Feb. 27, 2020

(65) Prior Publication Data
US 2021/0327563 A1    Oct. 21, 2021

Related U.S. Application Data

(60) Provisional application No. 62/720,229, filed on Aug. 21, 2018.

(51) Int. Cl.
*G16H 30/40* (2018.01)
*G06N 3/10* (2006.01)
(Continued)

(52) U.S. Cl.
CPC ............. *G16H 30/40* (2018.01); *G06N 3/105* (2013.01); *G06T 7/0012* (2013.01);
(Continued)

(58) Field of Classification Search
CPC ........ G16H 30/40; G06N 3/105; G06N 3/045; G06N 3/044; G06N 3/048; G06N 20/10;
(Continued)

(56) References Cited

U.S. PATENT DOCUMENTS 7,662,100 B2    2/2010  Murashita et al.
10,121,243 B2   11/2018 Boroczky et al.
(Continued)

FOREIGN PATENT DOCUMENTS

JP    2006346094 A    12/2006
WO    2017210690 A1   12/2017

OTHER PUBLICATIONS

International Search Report and Written Opinion for International Application No. PCT/EP2019/072323, filed Aug. 21, 2019, 14 pages.
(Continued)

*Primary Examiner* — Fayyaz Alam

(57) ABSTRACT

Various embodiments of the present disclosure are directed to a salient medical imaging controller (80) employing an artificial intelligence engine (40) and a graphical user interface (70). In operation, the artificial intelligence engine (40) includes one or more machine learning models (42) trained to render a feature assessment of a medical image. The graphical user interface (70) provides a user interaction with the artificial intelligence engine (40) to manipulate a salient visualization of the feature assessment of the medical image by the machine learning model(s) (42).

20 Claims, 28 Drawing Sheets

(51) Int. Cl.
*G06T 7/00* (2017.01)
*G06V 10/22* (2022.01)
*G06V 10/46* (2022.01)

(52) U.S. Cl.
CPC .......... *G06V 10/235* (2022.01); *G06V 10/462* (2022.01); *G06T 2200/24* (2013.01); *G06T 2207/20081* (2013.01); *G06V 2201/031* (2022.01)

(58) Field of Classification Search
CPC ...... G06N 20/20; G06N 3/084; G06T 7/0012; G06T 2200/24; G06T 2207/20081; G06T 19/00; G06T 2210/41; G06V 10/235; G06V 10/462; G06V 2201/031
See application file for complete search history.

(56) References Cited

U.S. PATENT DOCUMENTS

| | | | | |
|---|---|---|---|---|
| 11,749,413 B2* | 9/2023 | Takata | .................. | G16H 30/40 705/2 |
| 2014/0254922 A1* | 9/2014 | Wang | .................. | G06V 10/462 382/159 |

OTHER PUBLICATIONS

Holzinger, et al., "Machine Learning and Knowledge Extraction in Digital Pathology Needs an Integrative Approach", Integrative Machine Learning, LNAI 10344, pp. 13-50.
Kieffer, et al., "Convolutional Neural Networks for Histopathology Image Classification: Training vs. Using Pre-Trained Networks", 7th International Conference on Image Processing Theory, Tools and Applications (IPTA 2017), Nov. 28-Dec. 1, Montreal, 6 pages.
Korbar, et al., "Looking Under the Hood: Deep Neural Network Visualization to Interpret Whole-Slide Image Analysis Outcomes for Colorectal Polyps", 2017 IEEE Conference on Computer Vision and Pattern Recognition Workshops (CVPRW), pp. 69-75.
Qi, et al., "Embedding Deep Networks into Visual Explanations", Computer Vision and Pattern Recognition, Artificial Intelligence 2020, Dec. 14, 2020, 15 pages.
Samek, et al., "Explainable Artificial Intelligence: Understanding, Visualizing and Interpreting Deep Learning Models", Computer Science, Artificial Intelligence, Aug. 28, 2017, 8 pages.
Chattopadhay, et al., "Grad-CAM++: Generalized Gradient-based Visual Explanations for Deep Convolutional Networks", 2018 IEEE Winter Conference on Applications of Computer Vision (WACV), Lake Tahoe, NV, 2018, pp. 839-847.
Chakraborty, et al., "Interpretability of Deep Learning Models: A Survey of Results", 2017 IEEE SmartWorld, Ubiquitous Intelligence & Computing, Advanced & Trusted Computed, Scalable Computing & Communications, Cloud & Big Data Computing, Internet of People and Smart City Innovation (SmartWorld/SCALCOM/UIC/ATC/CBDCom/IOP/SCI), San Francisco, CA, 2017, pp. 1-6.
Wu, et al., "Interpretable R-CNN", Computer Science, Computer Vision and Pattern Recognition, Nov. 14, 2017, 13 pages.
Mobiny, et al., "Lung Cancer Screening Using Adaptive Memory-Augmented Recurrent Networks", Computer Science-Machine Learning, Oct. 2017, pp. 1-14.
Zeiler, et al., "Visualizing and Understanding Convolutional Networks", European Conference on Computer Vision, (ECCV) 2014, Lecture Notes in Computer Science, vol. 8689, pp. 818-833.
Selvaraju et al., "Grad-CAM: Visual Explanations from Deep Networks via Gradient-based Localization", 2017 IEEE International Conference on Computer Vision (ICCV), Venice, Italy, 2017, pp. 618-626.

* cited by examiner

SALIENT VISUAL EXPLANATIONS OF FEATURE ASSESSMENTS BY MACHINE LEARNING MODELS

RELATED APPLICATIONS

This application is the U.S. National Phase application under 35 U.S.C. § 371 of International Application No. PCT/EP2019/072323, filed on Aug. 21, 2019, which claims the benefit and priority to Provisional Application No. 62/720,229, filed Aug. 21, 2018, which is incorporated by referenced in its entirety.

TECHNICAL FIELD

Various embodiments described in the present disclosure relate to systems, machines, controllers and methods incorporating one or more machine learning models for rendering a feature assessment of a medical imaging of an anatomical region or an anatomical organ. More particularly, but not exclusively, various embodiments relate to providing a salient visual explanation of the feature assessment by the machine learning model(s) of the medical imaging of the anatomical region/organ.

BACKGROUND

Deep learning based artificial intelligence (AI) technologies have shown to provide promising results in medical imaging based diagnosis (e.g., deep learning diagnosis of an ultrasound (US) imaging, an X-ray imaging, a computed tomography (CT) imaging, a magnetic resonance imaging (MRI), a positron emission tomography (PET) imaging, a single photon emission computed tomography (SPECT) imaging and a diffuse optical tomography (DOT) imaging). Despite the promising results, most of such algorithms output only the highest risk and will face regulatory and clinical adoption challenges. To address this issue, in the deep learning community, a significant amount of effort has gone into the interpretability of deep neural networks for researchers. However, these approaches are optimized for deep learning practitioners rather than clinicians (e.g., physicians and radiologists) whereby many approaches exclusively focus on the visualization of the deep neural network itself while some other approaches try to explore the relationships between parts of the medical image and the probability of the medical image. Thus, currently components built for clinicians to interactively explore how a deep neural network works with medical images beyond the risk output are non-existent. Moreover, the image characteristics of medical images are different than natural image with diffuse, ill-defined structures and often 3D+ dimensions.

More particularly, one problem with the adoption of machine learning model based AI technologies in a medical domain is that machine learning models are often perceived as a "black box" by a clinician. Despite the proven performance of machine learning models in medical imaging based diagnosis, the non-transparent reasoning process of the machine learning models make it difficult for clinicians to understand how and why the model works. This is especially burdensome on a clinician because a computer aided diagnosis has not produced the gains that might be expected also in part due to poor interaction between the clinician and the AI. For example, because most cases in screening settings are negative, even a good AI will typically produce many more false positives than true positives. Consequently, the positive predictive value of the information is low. This reduces clinician trust and inhibits clinical adoption of AI that could save lives.

While some work has been done for visualizing predictions from two-dimensional (2D) convolutional neural networks (2D ConvNets) by presenting 2D localization maps (e.g., heatmaps), methods for visualization of predictions/classifications from three-dimensional (3D) convolutional neural networks (3D ConvNets) have proved to be difficult to develop. This is particularly true when the $3^{rd}$ dimension is either hidden or the most relevant angle and perspective is not known in advance. More particularly, 3D ConvNets are often used for computer-assisted diagnosis based on volumetric medical images (e.g., 3D US, 3D X-Ray, CT, MRI, PET, SPECT and DOT). Understanding the decision-making process of 3D ConvNets is critical for the well-trained clinician to confirm and admit the proposed prediction. Additionally, visualization of 3D localization maps (heatmaps) is challenging mostly because such maps from a last layer or an intermediate layer of a 3D ConvNet are (1) multidimensional (4D tensors), (2) low resolution as compared to the inputted volumetric medical image and (3) difficult to interpret using simple rendering techniques.

SUMMARY

According to the foregoing, various embodiments described in the present disclosure present a salient visualization technology that will allow machine learning model based feature assessment algorithms to 'explain' themselves to clinicians.

One set of embodiments of the present disclosure are directed to an "Explanation Through Salient Visualization" aspect of the present disclosure. More particularly, this aspect of the present disclosure provides various embodiments of graphical user interfaces providing user interaction with one or more machine learning model(s) providing a feature assessment of a medical imaging of a body, human or animal.

A first embodiment of this set of embodiments is a salient medical imaging controller employing a memory storing an artificial intelligence engine and a graphical user interface, wherein the artificial intelligence engine includes one or more machine learning models. The salient medical imaging controller further employs one or more processor(s) in communication with the memory with the processor(s) configured to (1) apply the machine learning model(s) to medical image data representative of one or more features of a medical image to render a feature assessment of the medical image, and (2) control a display of the graphical user interface providing a user interaction with the artificial intelligence engine to manipulate a salient visualization of the feature assessment of the medical image by machine learning model(s).

A second embodiment of this set of embodiments is a non-transitory machine-readable storage medium encoded with instructions for execution by one or more processors. The non-transitory machine-readable storage medium stores instructions to (1) apply an artificial intelligence engine including one or more machine learning models to medical image data representative of one or more features of a medical image to render a feature assessment of the medical image, and (2) control a display of a graphical user interface providing a user interaction with the artificial intelligence engine to manipulate a salient visualization of the feature assessment of the medical image by the machine learning model(s).

A third embodiment of this set of embodiments is salient medical imaging method involving (1) an application of an artificial intelligence engine including one or more machine learning models to medical image data representative of features of a medical image to render a feature assessment of the medical image, and (2) a controlling of a display of a graphical user interface providing a user interaction with the artificial intelligence engine to manipulate a salient visualization of the feature assessment of the medical image by the machine learning model(s).

For purposes of describing and claiming the present disclosure:

(1) the terms of the art of the present disclosure including, but not limited to, "medical imaging", "artificial intelligence engine", "data pre-processor", "machine learning model", "neural network", "support vector machine, "salient image manager", "medical image display engine", "image viewer", "medical image", "medical image generator", "salient image generator", "image reslicing", "image segmentation" and "graphical user interface" are to be broadly interpreted as known and appreciated in the art of the present disclosure and exemplary described in the present disclosure;

(2) the term "feature" broadly encompasses any type of object identifiable and/or characterizable within a medical image by one or more trained machine learning model(s) including, but not limited to, anatomical objects (e.g., vessels, organs, etc.), foreign objects (e.g., procedural tools/instruments and implanted devices) and image artifacts (e.g., noise, grating lobes);

(3) the term "feature assessment" broadly encompasses any type of prediction or classification of an identification and/or characterization of the feature;

(4) the term "salient image" broadly encompasses broadly encompasses an illustration of feature assessment. Examples of a salient image include, but are not limited to, a heatmap, a feature segmentation and an activation diagram;

(5) the term "salient visualization" broadly encompasses a display of one or more salient images;

(6) the term "controller" broadly encompasses all structural configurations, as understood in the art of the present disclosure and hereinafter conceived, of a main circuit board or an integrated circuit for controlling an application of various principles of the present disclosure as subsequently described in the present disclosure. The structural configuration of the controller may include, but is not limited to, processor(s), non-transitory machine-readable storage medium(s), an operating system, application module(s), peripheral device controller(s), slot(s) and port(s); and (7) "data" may be embodied in all forms of a detectable physical quantity or impulse (e.g., voltage, current, magnetic field strength, impedance, color) as understood in the art of the present disclosure and as exemplary described in the present disclosure for transmitting information and/or instructions in support of applying various principles of the present disclosure as subsequently described in the present disclosure. Data communication encompassed by the present disclosure may involve any communication method as known in the art of the present disclosure including, but not limited to, data transmission/reception over any type of wired or wireless datalink and a reading of data uploaded to a computer-usable/computer readable storage medium.

The foregoing embodiments and other embodiments of the present disclosure as well as various features and advantages of the present disclosure will become further apparent from the following detailed description of various embodiments of the present disclosure read in conjunction with the accompanying drawings. The detailed description and drawings are merely illustrative of the present disclosure rather than limiting, the scope of the inventions of present disclosure being defined by the appended claims and equivalents thereof.

BRIEF DESCRIPTION OF THE DRAWINGS

In order to better understand various example embodiments, reference is made to the accompanying drawings, wherein.

DETAILED DESCRIPTION

As will be further explained in detail in the present disclosure, the present disclosure is premised on a salient visualization technology that will allow machine learning model based feature assessment algorithms to 'explain' themselves to clinicians. For the present disclosure, a machine learning model may be any type of predicting machine learning model or any type of classifying machine learning model known in the art of the present disclosure including, but not limited to, a deep neural network (e.g., a convolutional neural network, a recurrent neural network, etc.) and a supervised learning machine (e.g., a linear or non-linear support vector machine, a boosting classifier, etc.).

Figure 1:
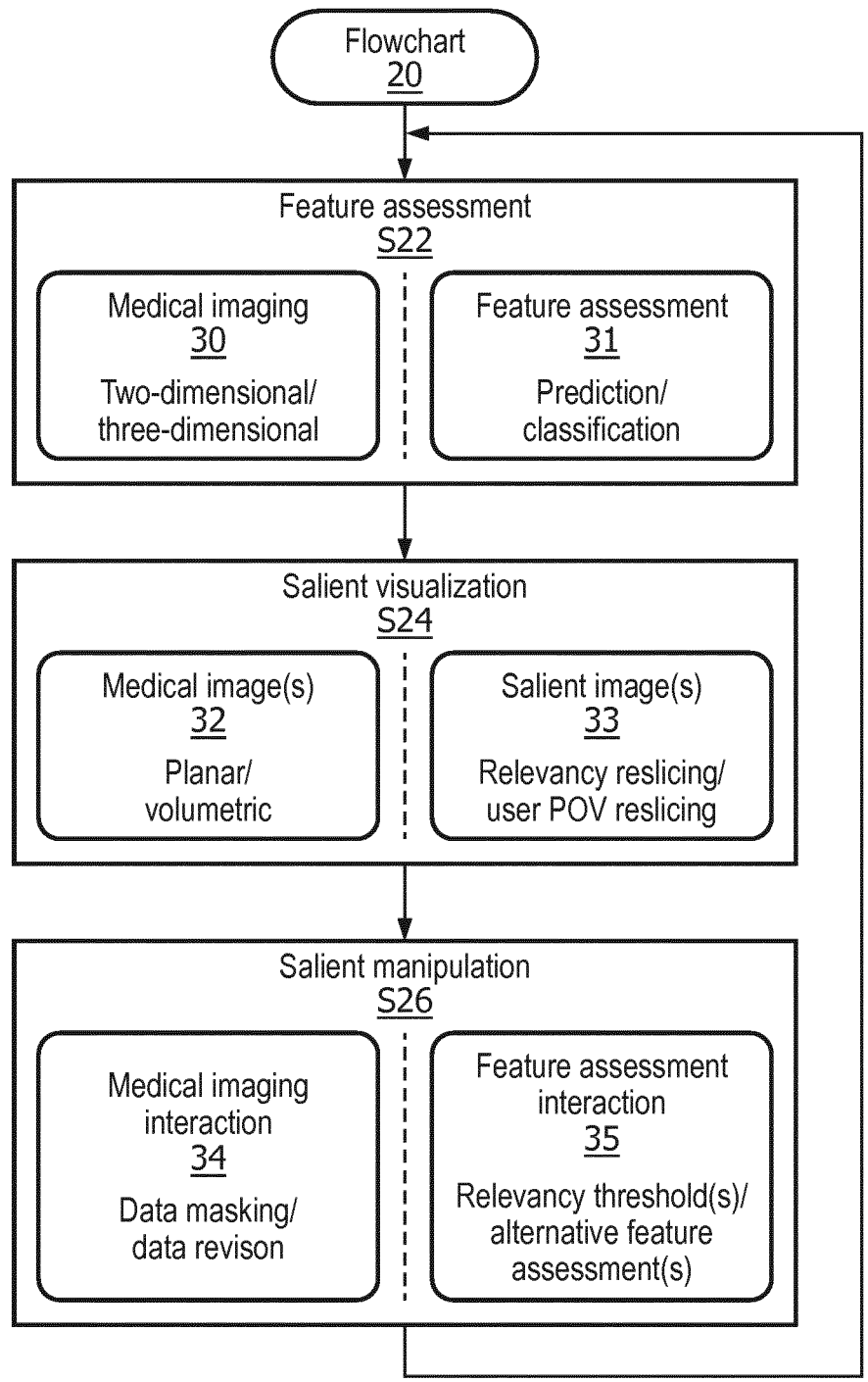
FIG. 1 illustrates exemplary embodiments of salient medical imaging method in accordance with the principles of the present disclosure.

To facilitate an understanding of the present disclosure, the following description of FIG. 1 teaches various embodiments of a salient visualization method of the present disclosure. From the description of FIG. 1, those having ordinary skill in the art of the present disclosure will appreciate how to apply the present disclosure for making and using numerous and various additional embodiments of salient visualization methods of the present disclosure.

Referring to FIG. 1, a salient medical imaging method 20 of the present disclosure implements a feature assessment stage S22, an salient visualization stage S24 and a salient manipulation stage 26.

Feature assessment stage S22 involves an application of an artificial intelligence engine including one or more machine learning models to a medical imaging 30 of a body, human or animal, to render a feature assessment 31 of the medical imaging 30.

In practice, medical imaging 30 encompasses a visualization of a portion or an entirety of a body for use in numerous and various procedures including, but not limited to, clinical diagnostic procedures, interventions/surgical procedures and patient monitoring. Examples of medical imaging 30 include, but are not limited to, two-dimensional (2D) medical imaging and three-dimensional (3D) medical imaging of an anatomical region/organ represented by raw imaging data generated by a medical imaging machine (e.g., 2D/3D US, 2D/3D X-Ray, CT, MRI, PET, SPECT and DOT) or represented by a medical image of the anatomical region/organ reconstructed from the raw imaging data.

In practice, feature assessment 31 encompasses a prediction or a classification of one or more features illustrated within the medical imaging of the body in terms of an identification and/or a characterization of the feature(s). More particularly, a feature encompasses any type of object identifiable and/or characterizable within a medical image by one or more trained machine learning models including, but not limited to, anatomical objects (e.g., vessels, organs, etc.), foreign objects (e.g., procedural tools/instruments and implanted devices) and image artifacts (e.g., noise, grating lobes).

Examples of a classification of a feature illustrated within the medical imaging 30 include, but are not limited to, classifying (1) anatomy (e.g., grey or white matter of the brain), (2) foreign objects (e.g., a guidewire, an implanted stent or valve), (3) lesion malignancy (e.g., skin lesion benign or malignant), (4) certain disease (e.g., positive or negative for diabetic retinopathy), (5) multi-categorical lesion classification (e.g. normal, glioblastoma, sarcoma and brain metastatic tumor), and (6) variances within a particular tissue (e.g., stenosis in a vessel, blood pooling in tissue/organ and tissue stiffness variances).

Examples of a prediction of a feature illustrated within the medical imaging 30 include, but are not limited to, predicting (1) whether a mass is non-cancerous (a negative diagnosis) or cancerous (a positive diagnosis), such as, for examples, risk scores for a lung nodule and (2) patient outcomes, such as, for example, a high chance and a low chance of a five-year disease-specific survival for instance of a patient diagnosed with colorectal cancer.

Still referring to FIG. 1, upon a rendering of feature assessment 31 during stage S22, salient visualization stage 24 involves a display of one or more medical images 32 and salient images 33.

In practice, a medical image 32 encompasses any type of image acquired by a medical imaging machine (e.g., a 2D/3D ultrasound machine, a 2D/3D X-ray machine, a CT machine, a MRI machine, a PET machine, a SPECT machine and a DOT machine). Examples of a medical image 32 include, but are not limited, to (1) an image frame or a video as acquired by a medical imaging machine, (2) an image segmentation of feature(s) illustrated within the medical imaging 30 and (3) an image overlay of an image frame/video acquired by one type of a medical imaging machine onto an image frame/video acquired by a different type of medical imaging machine (e.g., an overlay of an 2D ultrasound image onto a 2D/3D X-ray image). A medical image 32 may be displayed as a planar view or a volumetric view of the medical imaging 30.

In practice, a salient image 33 encompasses an illustration of feature assessment 31. Examples of a salient image 33 include, but are not limited to, a heatmap, a feature segmentation and an activation diagram.

As will be further described in the present disclosure, a heatmap encompasses a planar or a volumetric graphical representation of feature assessment 31 utilizing a color scheme (e.g., grayscale and visible spectrum) to highlight any relevancy differential between features to the feature assessment 31 of medical imaging 30.

As will be further described in the present disclosure, a feature segmentation encompasses a planar or a volumetric partitioning of feature(s) of a particular minimal relevancy to feature assessment 31 of medical imaging 30 whereby the feature(s) may be displayed individually or highlighted within a displayed medical image 32.

As will be further described in the present disclosure, an activation diagram encompasses a planar view of a n×m matrix of outputs of the machine learning model(s) (e.g., filtered outputs of neural networks) arranged in order of relevancy (e.g., left to right or up to down), n≥1 and m≥1.

During salient visualization stage 24, the present disclosure provides for a relevancy reslicing and a user specified reslicing of a volumetric salient image 33.

In practice, as will be further described in the present disclosure, a relevancy reslicing of a volumetric salient image encompasses a reslicing of a planar salient image from the volumetric salient image based on a relevancy level of each feature to a feature assessment 31 of the volumetric medical image by the machine learning model(s). More particularly, a salient voxel of a volumetric salient image has a relevancy level exceeding a relevancy threshold and a plurality of salient voxels will define a salient view of the assessed features of medical imagine 30. For reslicing purposes, a center point and an orientation of the resliced planar salient image within the volumetric salient image is derived from an intersection of a resliced salient plane with the volumetric salient image that includes one or more salient voxels.

In a first relevancy reslicing embodiment as will be further described in the present disclosure, the center point and the orientation of the resliced planar salient image within the volumetric salient image is derived from an intersection of a resliced salient plane with the volumetric salient image that includes a highest spatial distribution of salient voxels, a highest summation of salient voxels, or a highest average of salient voxels relative to a coordinate plane of the volumetric salient image.

In a second relevancy reslicing embodiment as will be further described in the present disclosure, the location and the orientation of the resliced planar salient image within the volumetric salient image is derived from an intersection of a resliced salient plane with the volumetric salient image based on a coordinate plane of the volumetric salient image (i.e., the XY plane, the XZ plane or the YZ plane). More particularly, the location and the orientation of the resliced planar salient image within the volumetric salient image is derived from an intersection of a resliced salient plane with the volumetric salient image that includes a highest spatial distribution salient voxels, a highest summation of salient voxels, or a highest average of salient voxels relative to the coordinate plane of the volumetric salient image.

In a third relevancy reslicing embodiment as will be further described in the present disclosure, a location and an orientation of the resliced planar salient image within the volumetric salient image is derived from an intersection of a resliced salient plane with the volumetric salient image based on a centroid of salient voxels. More particularly, the location and the orientation of the resliced planar salient image within the volumetric salient image is derived from an intersection of a resliced salient plane with the volumetric salient image that includes a highest spatial distribution salient voxels, a highest summation of salient voxels, or a highest average of salient voxels relative to the centroid of the salient voxels.

In practice, a user specified reslicing of a volumetric salient image encompasses a reslicing of a planar salient image from the volumetric salient image based on a user specified center point or orientation of the planar salient image includes one or more salient voxels. More particularly, the location and the orientation of the resliced planar salient image within the volumetric salient image is derived from an intersection of a resliced salient plane with the volumetric salient image that includes a highest spatial distribution salient voxels, a highest summation of salient voxels, or a highest average of salient voxels based on the user specified center point or orientation the planar salient image.

Still referring to FIG. 1, prior to an initial rendering of feature assessment 31 during stage S22 or subsequent to an initial display of images 32 or images 33, salient manipulation stage S26 involves a user interaction with the artificial intelligence engine, via a graphical user interface (GUI), to manipulate a salient visualization of the feature assessment 31 of medical imaging 30.

In practice, the salient visualization of feature assessment 31 of medical imaging 30 encompasses a static or an interactive display of salient image(s) 33 and optionally of medical images 32 in a manner supporting the underlying procedure, and the manipulation of the salient visualization of medical imaging 30 encompasses a medical imaging interaction 34 with the artificial intelligence engine to mask or revise medical imaging 30, or a feature assessment interaction 35 to vary relevancy thresholds for the features of medical imaging 40 or hypothesize alternative feature assessments 31 of medical imaging 30.

More particularly, in a data masking embodiment of medical imaging interaction 34 as will be further described in the present disclosure, a displayed GUI enables a clinician to interact with a planar medical image or a volumetric medical image directly and see how the artificial intelligence engine responds. For example, a clinician may analysis salient image(s) 33 to ascertain if one or more particular area(s) of a planar medical image or a volumetric medical image is(are) irrelevant to a current feature assessment 31. If the clinician suspects one or more particular area(s) of the planar medical image or the volumetric medical image is(are) irrelevant to a current feature assessment 31 of such image, then the clinician may mask the irrelevant area(s) and view the salient image(s) to see the impact such masking has on the feature assessment 31 of medical imaging 30.

In a data revision embodiment of medical imaging interaction 34 as will be further described in the present disclosure, a displayed GUI enables a clinician to test the influence of each input into the artificial intelligence engine on feature assessment 31 of medical imaging 30 as visualized by salient image(s) 30. Examples of a data revision include, but are not limited to, (1) an enabling/disabling a medical imaging input or a combination of medical imaging inputs of the artificial intelligence engine, (2) an increasing/decreasing the pixel/voxel intensity value of medical imaging input or a combination of medical imaging inputs of the artificial intelligence engine, (3) an enabling/disabling an auxiliary information input or a combination of auxiliary information inputs of the artificial intelligence engine, or (4) an altering an auxiliary information input or a combination of auxiliary information inputs of the artificial intelligence engine.

In a relevancy threshold embodiment of feature assessment interaction 35 as will be further described in the present disclosure, a displayed GUI enables a clinician setting of a relevance level of the pixels of a planar medical image to the feature assessment 31 of the planar medical image or a clinician setting of a relevance level of the voxels of a volumetric medical image to the feature assessment 31 of the volumetric medical image. The insight is that not all pixels of a planar medical image or all voxels of a volumetric planar image are equally relevant to the feature assessment 31 and clinicians typically focus on feature(s) of the image they think are most suspicious. As such, the relevancy level of pixels of a planar medical image or voxels of a volumetric planar image may be set by a clinician to a value so that a feature of the image will be more distinctively highlighted within the salient image(s) 33 if this feature reaches that level of relevance.

In an alternative feature assessment embodiment of feature assessment interaction 35 as will be further described in the present disclosure, a clinician may hypothesize between different predictions or different classifications of the feature assessment 31 of medical imaging 30 (e.g., prediction/classification x and prediction/classification y), and if the artificial intelligence engine renders prediction/classification x of medical imaging 30 as visualized by salient image(s) 31 illustrative of prediction/classification x of medical imaging 30, then the clinician may select prediction/classification y via the GUI to see the features that are most relevant to prediction/classification y of medical imaging 30 as visualized by salient image(s) 31 illustrative of prediction/classification y of medical imaging 30.

In practice, medical imaging interaction 34 and feature assessment interaction 35 may be utilized individually or in combination.

Flowchart 20 will continually conditionally loop through stages S22-S26 until an associated procedure or a related phase of the associated procedure is terminated.

Figure 2A:
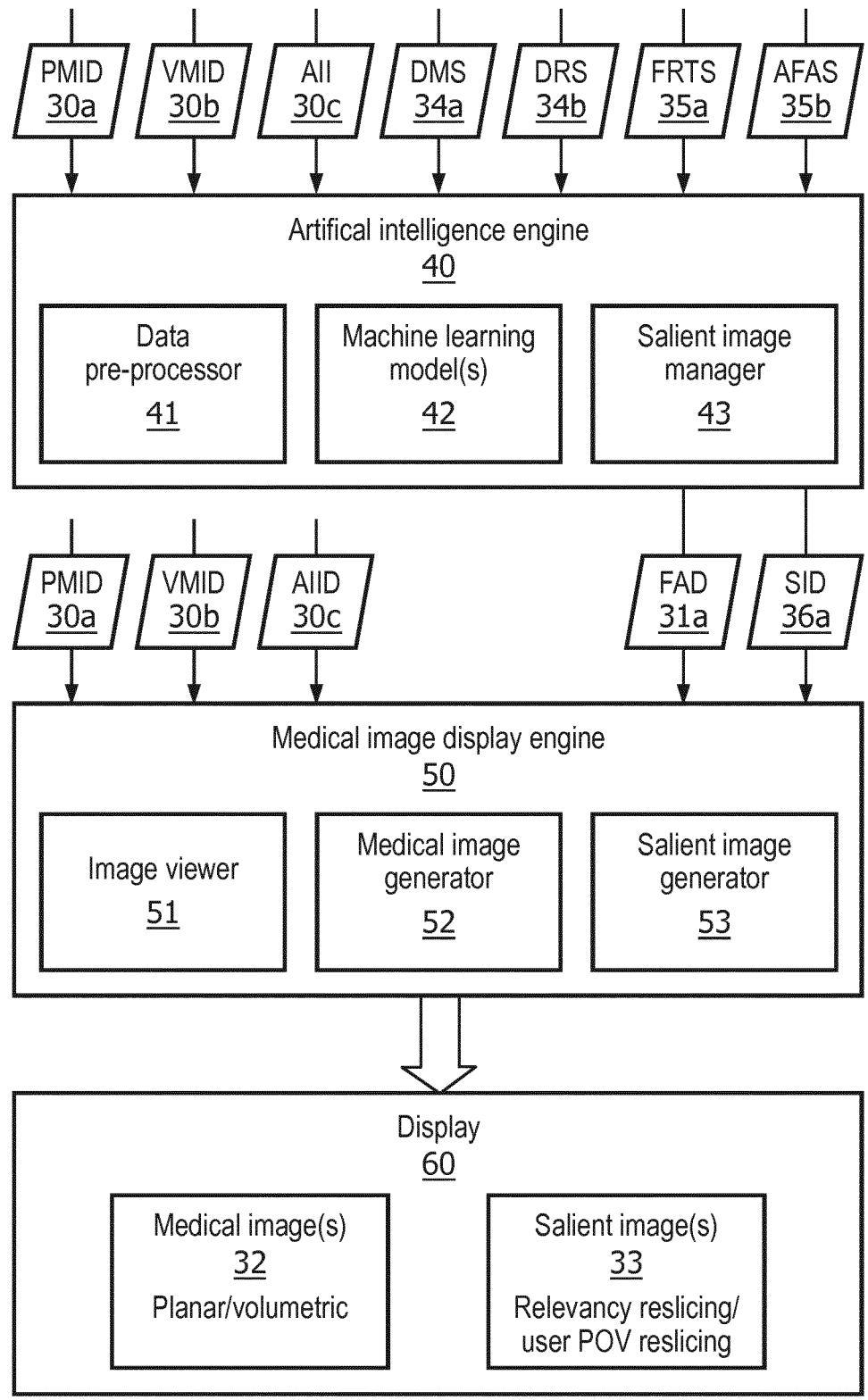
FIG. 2A illustrates exemplary embodiments of an artificial intelligence engine and medical image display engine in accordance with the principles of the present disclosure.
Figure 2B:
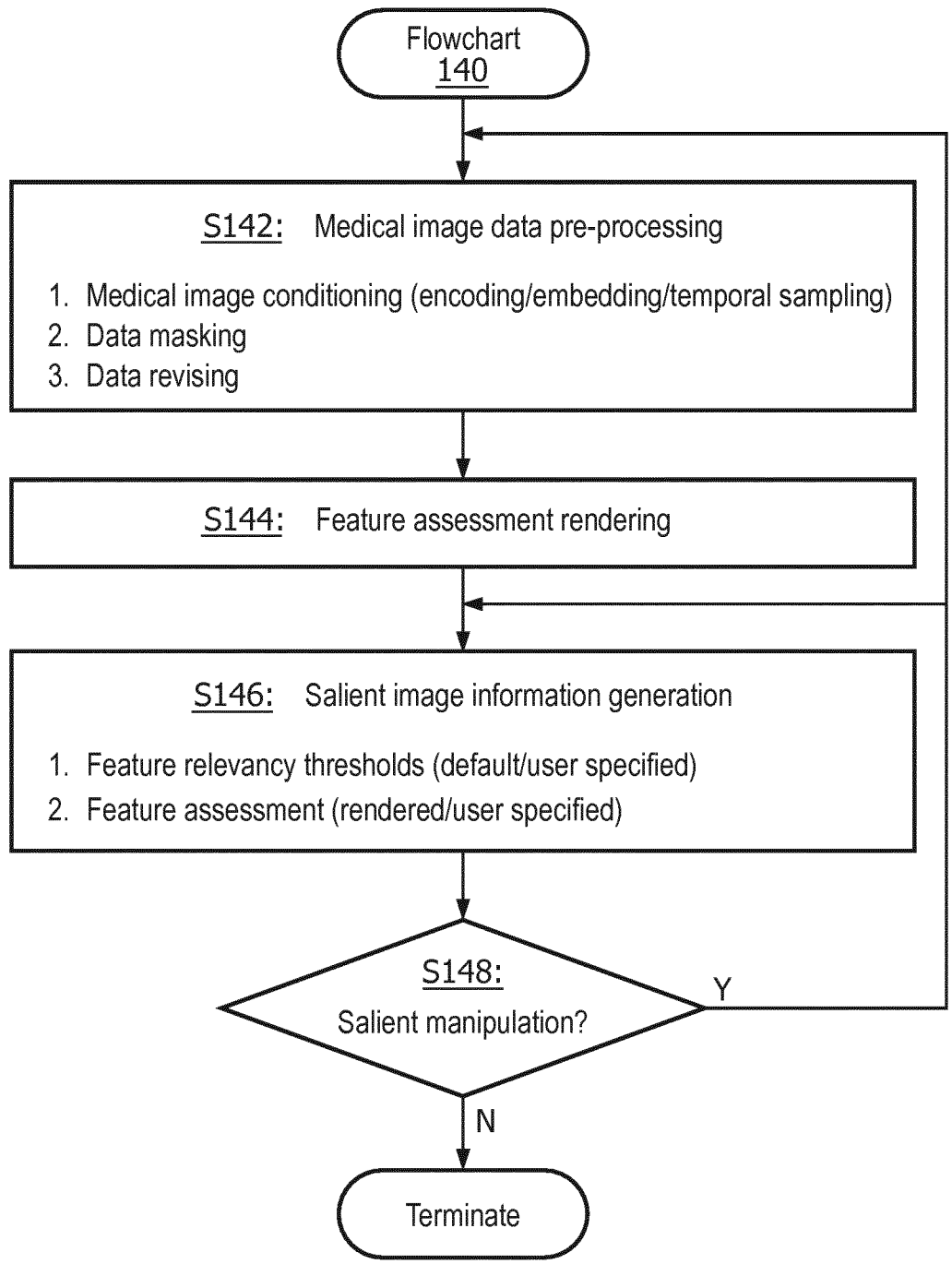
FIG. 2B illustrates a feature assessment method in accordance with the principles of the present disclosure.
Figure 2C:
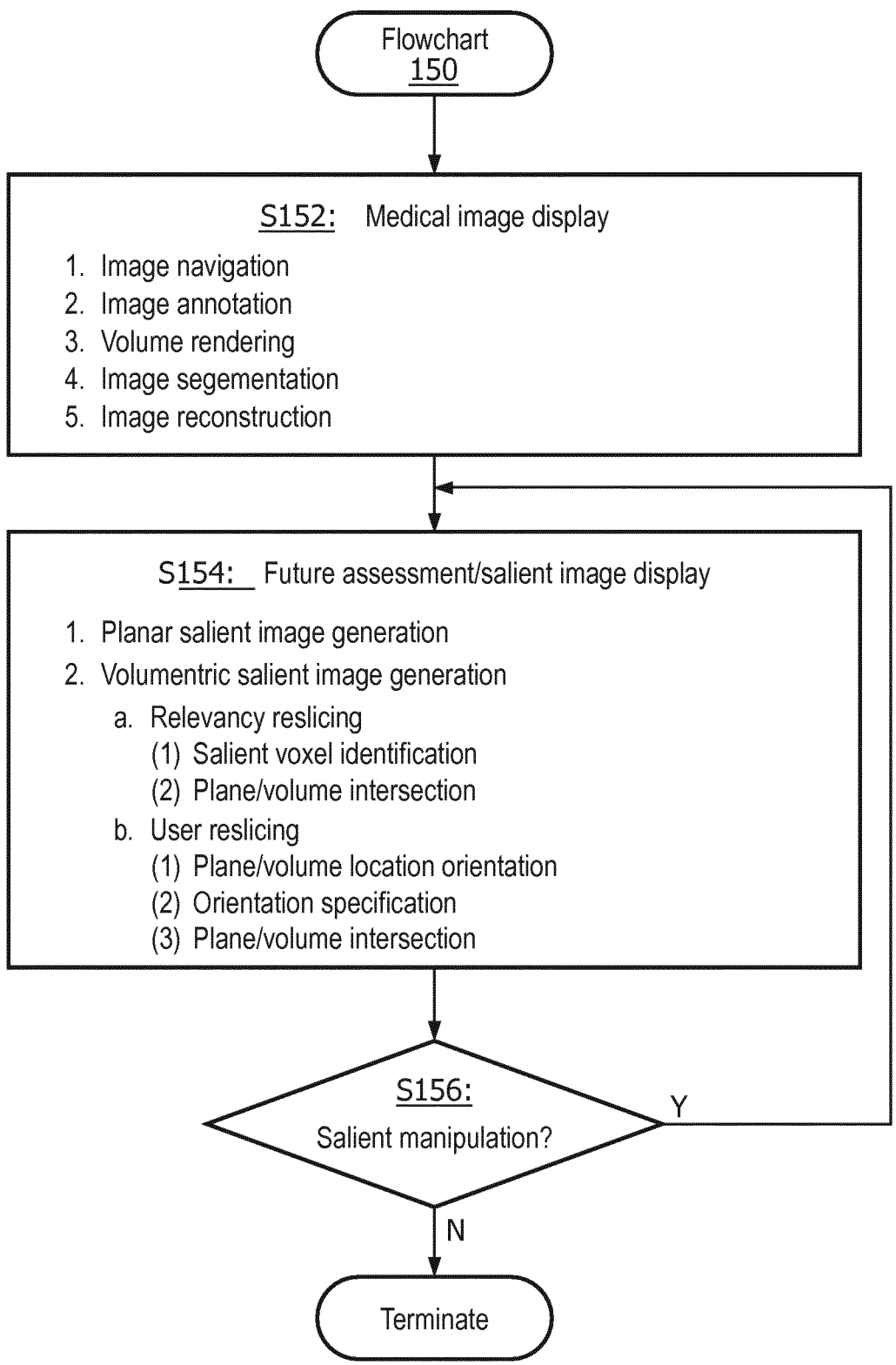
FIG. 2C illustrates a salient visualization method in accordance with the principles of the present disclosure.

To facilitate a further understanding of the present disclosure, the following description of FIGS. 2A-2C teach various embodiments of an artificial intelligence engine and a medical image display engine of the present disclosure. From the description of FIGS. 2A-2C, those having ordinary skill in the art of the present disclosure will appreciate how to apply the present disclosure for making and using numerous and various additional embodiments of artificial intelligence engines and medical image display engines of the present disclosure.

Referring to FIG. 2A, artificial intelligence engine 40 renders a feature assessment 31 of medical imaging 30 as previously described for stage S22 of FIG. 1. To this end, artificial intelligence engine 40 includes a data pre-processor 41, one or more machine learning models 42 and a salient image manager 43 for implementation of a feature assessment method represented by a flowchart 140 of FIG. 2B.

Referring to both FIGS. 2A and 2B, data pre-processor 41 processes planar medical imaging data 30a or volumetric medical imaging data 30b during a stage S142 of flowchart 140 by inputting data 30a/30b into the machine learning model(s) 42 to thereby render a feature assessment 31a during a stage S144 of flowchart 140. Additionally, data pre-processor 41 may further process auxiliary imaging information 30c from a medical imaging machine (e.g., 2D/3D ultrasound machine, 2D/3D X-ray machine, CT machine, MRI machine, PET machine, SPECT machine and DOT machine) related to planar medical imaging data 30a or volumetric medical imaging data 30b (e.g., a radius and/or a sphericity of an anatomical organ segmented from reconstructed medical image 132a) for inputting information 30c into the machine learning model(s) 42 to thereby render the feature assessment 31a during a stage S144. Auxiliary imaging information 30c may further include information related to the patient in terms of age, gender and health history. Examples of processing medical image data 30a/30b and auxiliary imaging information 30c by data pre-processor 25 include, but are not limited to, an encoding, an embedding or a temporal sampling of the medical image data medical image data 30a/30b and auxiliary imaging information 30c.

In practice, data pre-processor 41 may be omitted from AI engine 40 if such pre-processing is unnecessary or previously performed prior to transmission of medical image data medical image data 30a/30b and optional auxiliary imaging information 30c to AI engine 40.

Referring back to FIG. 2A, a machine learning model 42 is a classifying machine learning model or a predicting machine learning model including, but not limited to, (1) a deep neural network (e.g., a convolutional neural network, a recurrent neural network, etc.) and (2) a supervised learning machine (e.g., a linear or nonlinear support vector machine, a boosting classifier, etc.). In practice, a machine learning model 43 may be trained to render feature assessment 31a of medical imaging 30a/30b for any type of medical procedure, any type of medical imaging machine or any type of patient, or alternatively may be trained to render a feature assessment of medical imaging data 30a/30b for one or more particular medical procedures or one or more particular type of medical imaging machines whereby the machine learning model 43 may be further trained for one or more particular types of patient. Also in practice, AI engine 40 may include a single machine learning model 42 or a plurality of similar and/or dissimilar machine learning models 42 including, but not limited to, (1) a distributed arrangement of individual machine learning models 42, (2) a network of two or more similar and/or dissimilar deep neural networks or (3) a network of two or more similar and/or dissimilar supervised learning machines.

Referring to both FIGS. 2A and 2B, the machine learning model(s) 42 of AI engine 40 input the (pre-processed) medical imaging data 30a/30b to render a feature assessment 31a of the medical imaging data 30a/30b during a stage S144 of flowchart 140 as previously described for feature assessment stage S22 of FIG. 1. Upon an initial execution of stage S144, during a stage S146 of flowchart 140, salient image manager 43 generates salient image data 36a representative of the relevance of each feature of medical imaging data 30a/30b to feature assessment 31a.

In practice, salient image data 36a is representative of the relevance of each feature of masked/revised medical imaging data 30a/30b to the new feature assessment 31a. In one embodiment for any type of machine learning model, salient image data 36a provides a scaling of each pixel represented by planar medical imaging data 30a and each voxel of volumetric medical imaging data 40a from least relevant pixel(s)/voxel(s) (e.g., 0) to most relevant pixel(s)/voxel(s) (e.g., 169). The scaling enables salient image generator 51 to generate a heatmap or a feature map. In a second embodiment particularly for neural networks, scaling image data 36a provides filter outputs ranging from least relevant filter output(s) to most relevant filter output(s).

More particularly, a deep neural network encompass multiple layers of activation neurons (i.e., feature elements) interconnected and trained for feature extraction and transformation to thereby calculate complex mappings between (pre-processed) medical imaging data 30a/30b (e.g., 2D pixels or 3D voxels)/auxiliary information 30c (if applicable) and a prediction or a classification via one or more output neurons (i.e., prediction elements). Each activation neuron applies a nonlinear activation function to a weighted linear combination of inputs (e.g., 2D pixels, 3D voxels, an upstream activation neuron output or a downstream activation neuron output). As such, the parameters of importance to a deep neural network are the structure of the connective neuron network, the nonlinear activation functions and weights of the activation neurons. Also of importance is a capability to execute any type of relevancy mapping for ascertaining an explanation of the prediction or the classification whereby such relevancy mapping may be used to generate salient image data 36a of the present disclosure (e.g., back propagation, guided back propagation, deconvolution, class activation mapping, gradient class activation mapping, etc.). For example, detected class activations may be projected back through the network to the input pixel/voxel space to detect which parts of the input medical image 30a/30b were most relevant to the prediction or classification.

For deep neural network embodiment of machine learning model(s) 42, salient image manager 43 executes the aforementioned relevancy mapping based on default feature relevancy thresholds for each activation to thereby generate the salient image data 36a for the rendered feature assessment 31a.

Furthermore, a support vector machine as known in the art of the present disclosure encompasses support vectors trained for delineating a hyperplane (i.e., prediction element) for linearly or nonlinearly separating feature vectors (i.e., feature elements) of medical imaging data 30a/30b (e.g., 2D pixels or 3D voxels) auxiliary information 30c (if applicable) into one of two classes. Linear support vector machines in particular learn a linear discriminant function whereby weights of the linear discriminant function may be utilized to assign a score to each 2D pixel or 3D voxel to thereby support a rendering of feature assessment 31a.

For support vector machine embodiments of machine learning model(s) 42, salient image manager 43 may utilize the 2D pixel/3D voxel scoring in conjunction with a nearest neighbor algorithm relative to the default feature relevancy thresholds to thereby generate the salient image data 36a for the rendered feature assessment 31a.

Still referring to FIGS. 2A and 2B, upon generation of salient information data 36a during stage S146, salient image manager 43 proceeds to a stage S148 of flowchart 140 whereby salient image manager 43 returns to stage S142 upon receipt of data masking specification 34a or data revising specification 34b or to stage S146 upon receipt of feature relevancy threshold specification 35a or alternative feature assessment specification 35b.

More particularly, if masking specification 34a or data revising specification 34b are received by salient image manager 43 via a GUI as will be further described in the present disclosure, then salient image manager 43 directs data pre-processor 41 to perform a data masking of planar medical image data 30a or volumetric medical image data 30b as directed by data masking specification 34a as previously described for salient manipulation stage S26 of FIG. 1, or a data revision of planar medical image data 30a or volumetric medical image data 30b as directed by data masking specification 34a as previously described for salient manipulation stage S26 of FIG. 1. Subsequently, stage S144 is repeated to render a new feature assessment 31a based on the data masking or the data revisions, and stage S146 is repeated to generate new salient image data 36a representative of the relevance of each feature of masked/revised medical imaging data 30a/30b to the new feature assessment 31a.

Furthermore, if feature relevancy threshold specification 35a or alternative feature assessment specification 35b are received by salient image manager 43 via a GUI as will be further described in the present disclosure, then salient image manager 43 generates salient image data 36a based on the feature relevancy thresholds specified by feature relevancy threshold specification 35a as previously described for salient manipulation stage S26 of FIG. 1 or the alternative feature assessment specified by alternative feature assessment specification 35b as previously described for salient manipulation stage S26 of FIG. 1.

Flowchart 140 will continually conditionally loop through stages S142-S148 until an associated procedure or a related phase of the associated procedure is terminated.

FIGS. 3A-3J illustrate exemplary examples of trained convolutional neural network (CNN) to render a feature assessment of a prediction or a classification of planar medical image data 30a or volumetric medical image data 30b. For each example, the convolutional neural networks employ one or more convolution/rectified linear unit (ReLU)/pooling layers and a fully connected layer to thereby output the feature assessment (e.g., a convolutional neural network (CNN) having four (4) convolutional layers trained to provide a particular type of prediction including, but not limited to, tumor classification, vessel segmentation, etc.). Alternatively, a fully connected layer of a CNN is connected to or replaced with a support vector machine (CNN/SVM).

In practice, a CNN of the present disclosure is trained on 2D or 3D medical imaging of a body encompassing the entire range of prediction scores of entire set of classifications Additionally, a CNN of the present disclosure are structured to output salient image data for purposes of generating a planar salient image or a volumetric salient image as will be further explained in the present disclosure. In particular, salient image data is filter outputs of the last convolutional layer of the CNN.

Furthermore in practice, a CNN of the present disclosure may process medical imaging interaction data indicative of (1) a clinician masking of area of medical planar medical image or a medical volumetric medical image to see the impact of data masking on the feature assessment as previously described for stage S26 of FIG. 1, or (2) clinician enabling/disabling and/or variance of image and auxiliary information inputs to the CNN to see the impact of data revision on the feature assessment as previously described for stage S26 of FIG. 1.

Additionally in practice, a CNN of the present disclosure may process feature assessment interaction data indicative of (1) a clinician setting of relevancy levels of the pixels of the planar medical imaging data or the voxels of the volumetric medical imaging for generating salient image(s) as previously described for stage S26 of FIG. for (2) indicative of a clinician selection between different hypotheses (e.g., x and y) as previously described for stage S26 of FIG. 1.

Figure 3A:
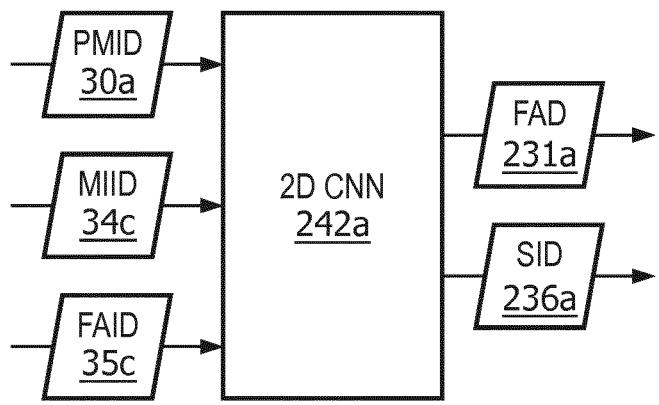
FIG. 3A illustrates an exemplary embodiment of a two-dimensional (2D) convolutional neural network (CNN) in accordance with the principles of the present disclosure.

In one embodiment of AI engine 40 as shown in FIG. 3A, a 2D CNN 242a is trained as known in the art of the present disclosure on a varied of classes of interpreted medical images of prior patients to render a feature assessment 231a of the medical imaging of a body represented by planar medical imaging data 30a. Additionally, 2D CNN 242a is operated via a relevancy mapping by salient image manager 43 to output 2D salient image data 236a for purposes of generating a planar salient image illustrative of feature assessment 231a (e.g., a 2D heatmap, a 2D feature map or an activation map). Further, 2D CNN 242a is operated via GUI(s) as previously described in the present disclosure in accordance with medical imaging interaction data 34c or feature assessment interaction data 35c.

Figure 3B:
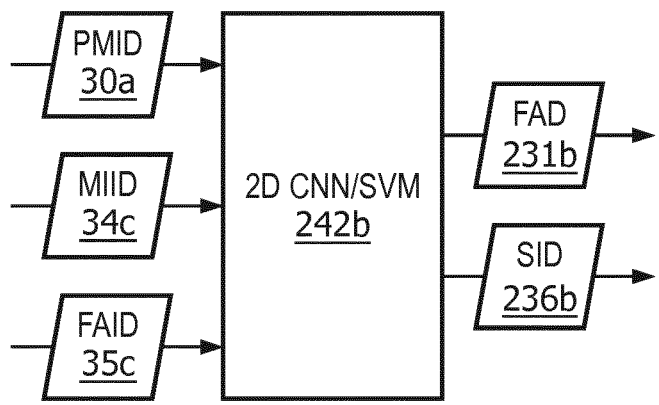
FIG. 3B illustrates an exemplary embodiment of a two-dimensional (2D) convolutional neural network/support vector machine (CNN/SVM) in accordance with the principles of the present disclosure.

In a second embodiment of AI engine 40 as shown in FIG. 3B, a 2D CNN/SVM 242b is trained as known in the art of the present disclosure on a varied of classes of interpreted medical images of prior patients to render a feature assessment 231b of the medical imaging of a body represented by planar medical imaging data 30a. Additionally, 2D CNN/SVM 242b is operated via a relevancy mapping by salient image manager 43 to output 2D salient image data 236b for purposes of generating a planar salient image illustrative of feature assessment 231b (e.g., a 2D heatmap, a 2D feature map or an activation map). Further, 2D CNN/SVM 242b is operated via GUI(s) as previously described in the present disclosure in accordance with medical imaging interaction data 34c or feature assessment interaction data 35c.

Figure 3C:
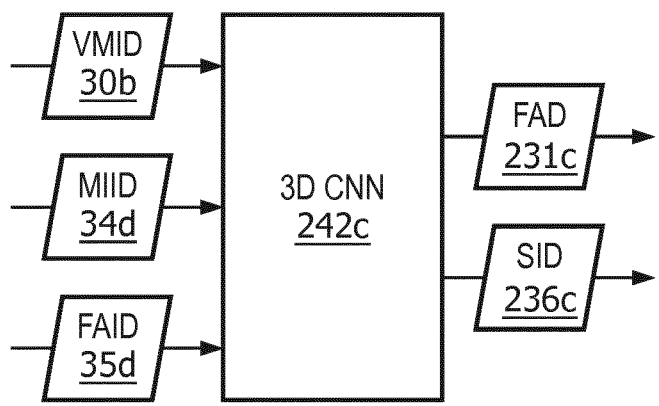
FIG. 3C illustrates an exemplary embodiment of a 3D CNN in accordance with the principles of the present disclosure.

In a third embodiment of AI engine 40 as shown in FIG. 3C, a 3D CNN 242c is trained as known in the art of the present disclosure on a varied of classes of interpreted medical images of prior patients to render a feature assessment 231c of the medical imaging of a body represented by volumetric medical imaging data 30b. Additionally, AI engine 242c is operated via a relevancy mapping by salient image manager 43 to output 2D salient image data 236c for purposes of generating a volumetric salient image illustrative of feature assessment 231c (e.g., a 3D heatmap, a 3D feature map or an activation map). Further, 3D CNN 242c is operated via GUI(s) as previously described in the present disclosure in accordance with medical imaging interaction data 34d or feature assessment interaction data 35d.

Figure 3D:
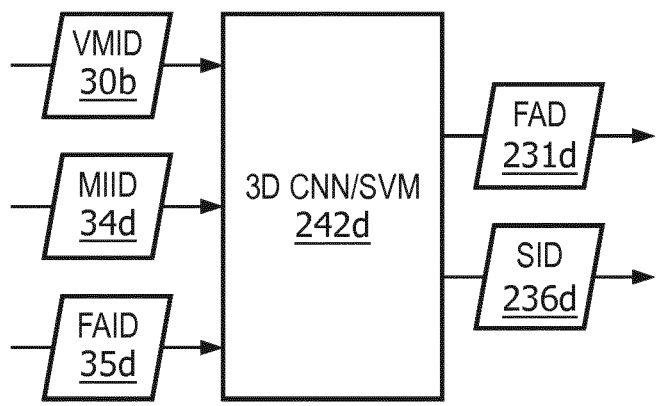
FIG. 3D illustrates an exemplary embodiment of a 3D CNN/SVM in accordance with the principles of the present disclosure.

In a fourth embodiment of AI engine 40 as shown in FIG. 3D, a 3D CNN/SVM 242d is trained as known in the art of the present disclosure on a varied of classes of interpreted medical images of prior patients to render a feature assessment 231d of the medical imaging of a body represented by volumetric medical imaging data 30b. Additionally, 3D CNN/SVM 242d is operated via a relevancy mapping by salient image manager 43 to output 2D salient image data 236d for purposes of generating a volumetric salient image illustrative of feature assessment 231d (e.g., a 3D heatmap, a 3D feature map or an activation map). Further, 3D CNN/SVM 242d is operated via GUI(s) as previously described in the present disclosure in accordance with medical imaging interaction data 34d or feature assessment interaction data 35d.

Figure 3E:
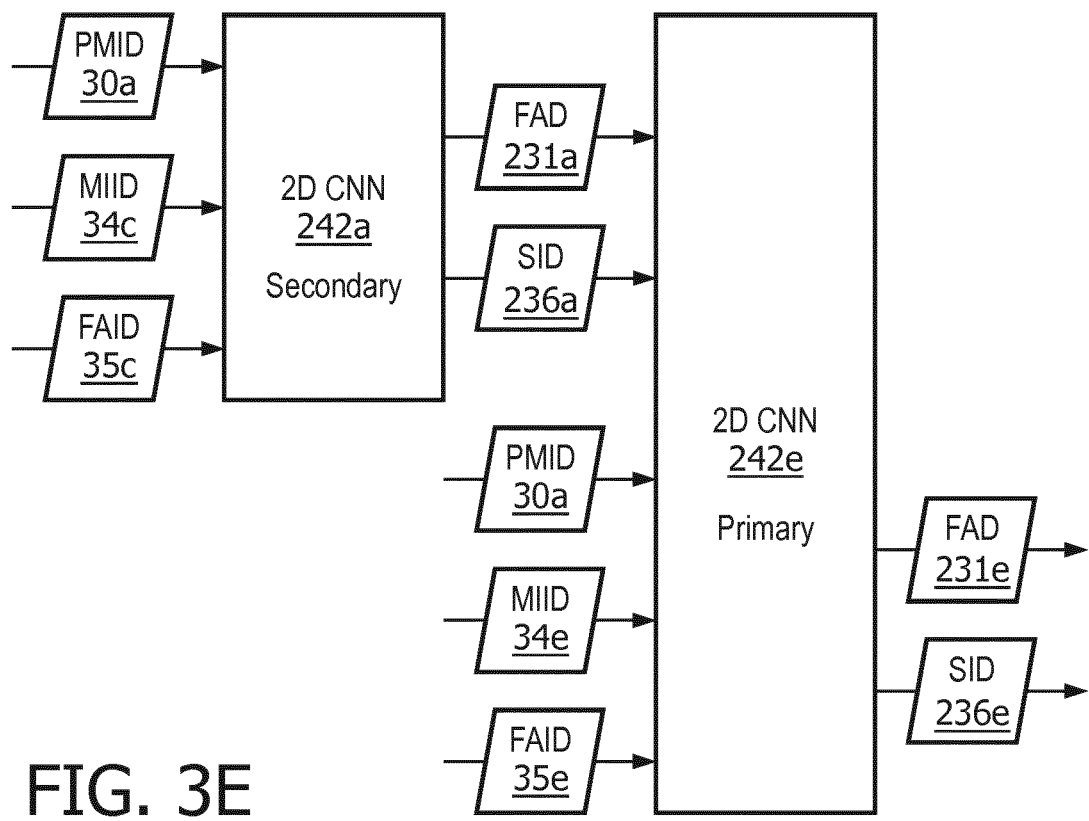
FIG. 3E illustrates an exemplary embodiment of a series network of 2D CNNs in accordance with the principles of the present disclosure.

In a fifth embodiment of AI engine 40 as shown in FIG. 3E, 2D CNN 242a (FIG. 3A) serves as a secondary CNN providing feature assessment 231a and salient image data 236 as inputs to a 2D CNN 242e serving as a primary CNN. 2D CNN 242e is trained as known in the art of the present disclosure on a varied of classes of interpreted medical images of prior patients and feature assessment 231a to render a feature assessment 231e of the medical imaging of a body as represented by volumetric medical imaging data 30b. Additionally, 2D CNN 242e is operated via a relevancy mapping by salient image manager 43 to output 2D salient image data 236e for purposes of generating a planar salient image illustrative of feature assessment 231a (e.g., a 2D heatmap, a 2D feature map or an activation map). Further, 2D CNN 242e is operated via GUI(s) as previously described in the present disclosure in accordance with medical imaging interaction data 34e or feature assessment interaction data 35e.

Figure 3F:
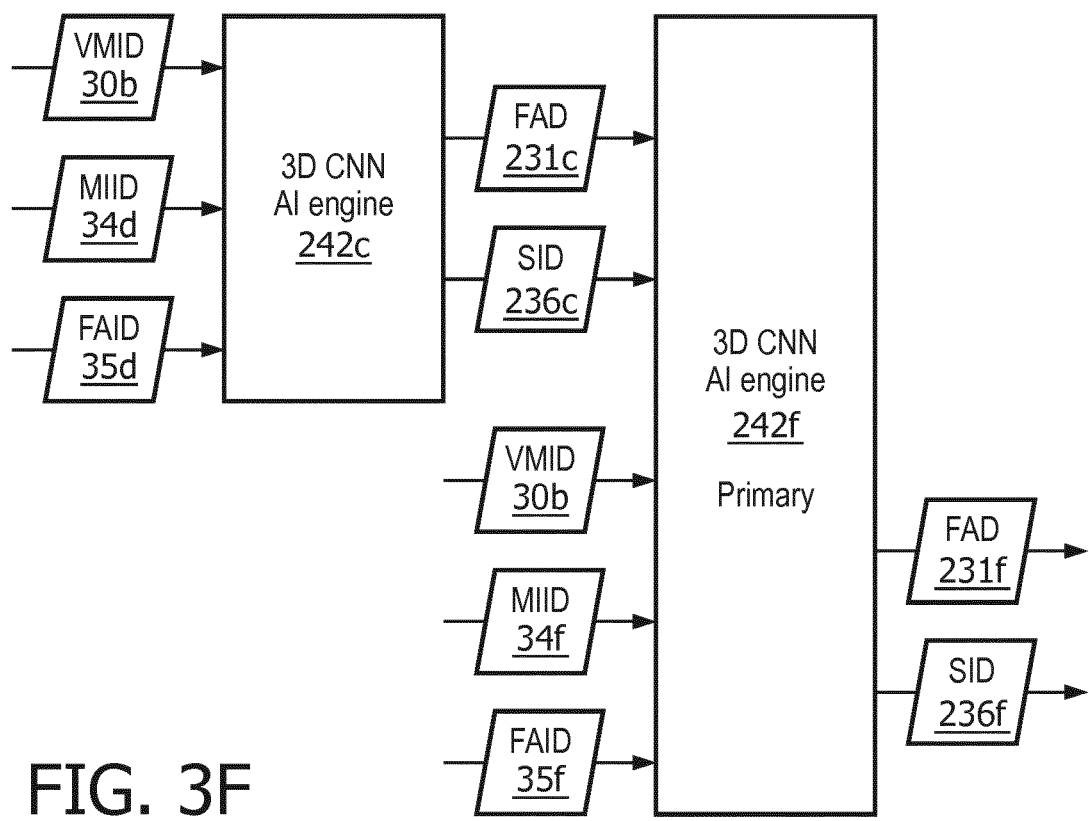
FIG. 3F illustrates an exemplary embodiment of a series network of 3D CNNs in accordance with the principles of the present disclosure.

In a sixth embodiment of AI engine 40 as shown in FIG. 3F, 3D CNN 242c (FIG. 3C) serves as a secondary CNN providing feature assessment 231c and salient image data 23c as inputs to a 3D CNN 242f serving as a primary CNN. 3D CNN 242f is trained as known in the art of the present disclosure on a varied of classes of interpreted medical images of prior patients and feature assessment 231c to render a feature assessment 231f of the medical imaging of a body represented by volumetric medical imaging data 30b. Additionally, 3D CNN 242f is operated via a relevancy mapping to output 3D salient image data 236f for purposes of generating a volumetric salient image illustrative of feature assessment 231f (e.g., a 3D heatmap, a 3D feature map or an activation map). Further, 3D CNN 242f is operated via GUI(s) as previously described in the present disclosure in accordance with medical imaging interaction data 34f or feature assessment interaction data 35f.

Figure 3G:
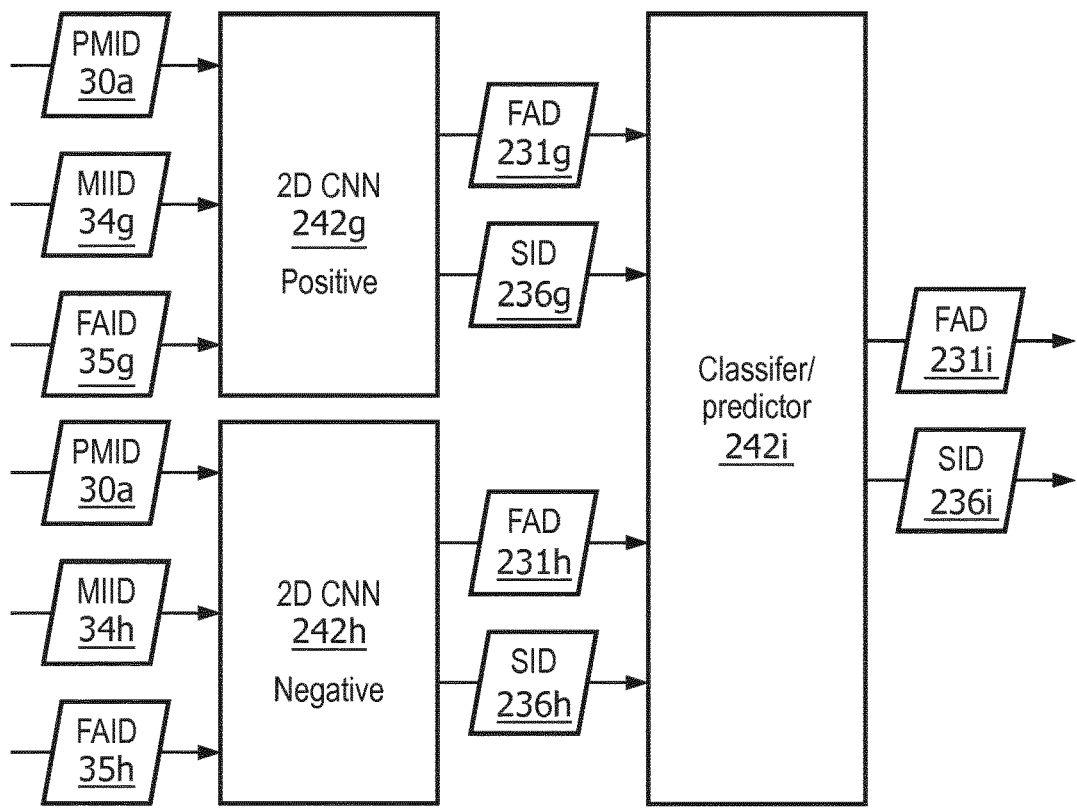
FIG. 3G illustrates a first exemplary embodiment of a parallel network of 2D CNNs in accordance with the principles of the present disclosure.

In a seventh embodiment of AI engine 40 as shown in FIG. 3G, a 2D CNN 242g is trained as known in the art of the present disclosure on class of positively interpreted medical images of prior patients (e.g., images of cancerous patients, images of a presence of a surgical tool within an anatomical region, etc.) to render a preliminary feature assessment 231g of the medical imaging of a body represented by planar medical imaging data 30a. Additionally, 2D CNN 242g is operated via a relevancy mapping by salient image manager 43 to output 2D salient image data 236g for purposes of generating a planar salient image illustrative of feature assessment 231g (e.g., a 2D heatmap, a 2D feature map or an activation map). Further, 2D CNN 242g is operated via GUI(s) as previously described in the present disclosure in accordance with medical imaging interaction data 34g or feature assessment interaction data 35g.

Still referring to FIG. 3G, 2D CNN 242h is trained as known in the art of the present disclosure on class of negatively interpreted medical images of prior patients (e.g., images of non-cancerous patients, images of an absence of a surgical tool within an anatomical region, etc.) to render a preliminary feature assessment 231h of the medical imaging of a body represented by planar medical imaging data 30a. Additionally, 2D CNN 242h is operated via a relevancy mapping by salient image manager 43 to output 2D salient image data 236h for purposes of generating a planar salient image illustrative of feature assessment 231h (e.g., a 2D heatmap, a 2D feature map or an activation map). Further, 2D CNN 242h is operated via GUI(s) as previously described in the present disclosure in accordance with medical imaging interaction data 34h or feature assessment interaction data 35h.

Still referring to FIG. 3G, a classifier/predictor 242i is structured to generate a final feature assessment 231i of the medical imaging of a body represented by planar medical imaging data 30a. In practice, classifier/predictor 242i may implement any technique as known in the art of the present disclosure for combining preliminary feature assessment 231g and preliminary feature assessment 231h to render a final feature assessment 231i. In one embodiment, classifier/predictor 242i may average risk scores associated with preliminary feature assessment 231g and preliminary feature assessment 231h to thereby render final feature assessment 231i. In a second embodiment, classifier/predictor 242i may implement a fully connected layer on behalf of networks 242g and 242h.

Still referring to FIG. 3G, classifier/predictor 242i is further structured to output salient image data 236i for purposes of generating a planar salient image illustrative of feature assessment 231i (e.g., a 2D heatmap, a 2D feature map or an activation map). In practice, classifier/predictor 242i may implement any technique as known in the art of the present disclosure for combining filter outputs of the convolutional layers of networks 242g and 242h to produce salient image data 236i illustrative of feature assessment 231i (e.g., a 2D heatmap, a 2D feature map or an activation map). In one embodiment, classifier/predictor 242i may average the filter outputs of the last convolutional layers of networks 242g and 242h to produce salient image data 236i.

Figure 3H:
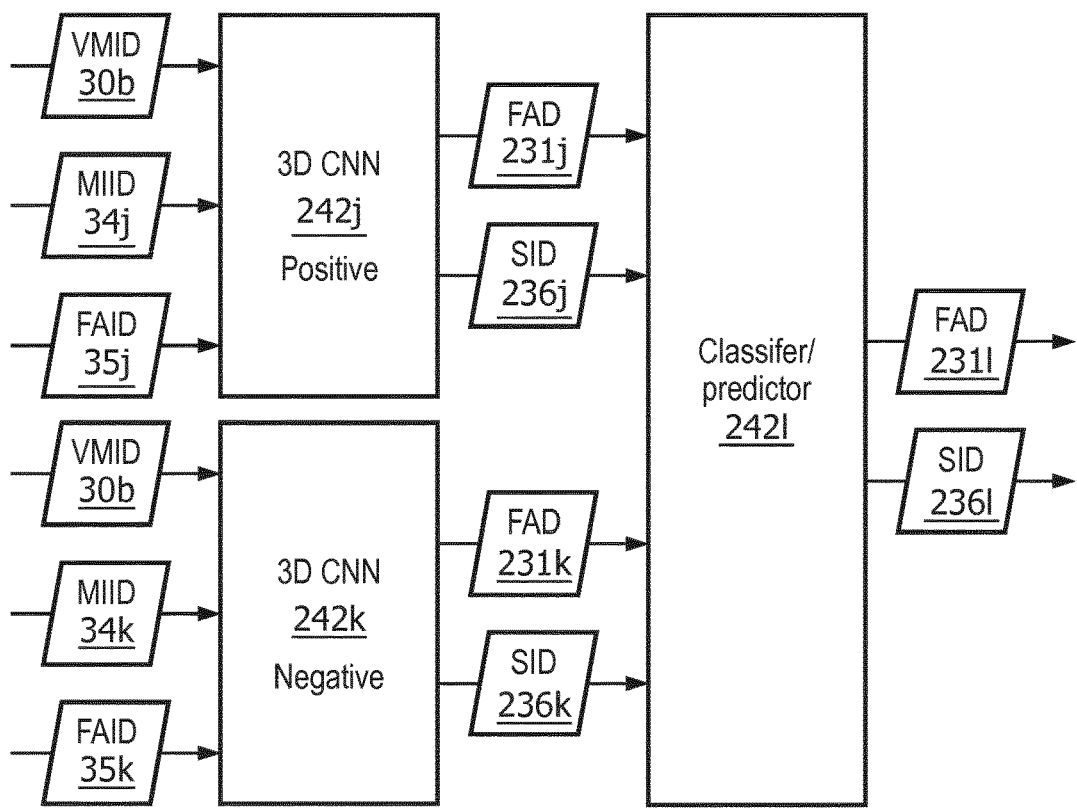
FIG. 3H illustrates a first exemplary embodiment of a parallel network of 3D CNNs in accordance with the principles of the present disclosure.

In an eighth embodiment of AI engine 40 as shown in FIG. 3H, a 3D CNN 242j is trained as known in the art of the present disclosure on class of positively interpreted medical images of prior patients (e.g., images of cancerous patients, images of a presence of a surgical tool within an anatomical region, etc.) to render a preliminary feature assessment 231j of the medical imaging of a body represented by volumetric medical imaging data 30b. Additionally, 3D CNN 242j is operated via a relevancy mapping by salient image manager 43 to output 3D salient image data 236j for purposes of generating a volumetric salient image illustrative of feature assessment 231j (e.g., a 3D heatmap, a 3D feature map or an activation map). Further, 3D CNN 242j is operated via GUI(s) as previously described in the present disclosure in accordance with medical imaging interaction data 34j or feature assessment interaction data 35j.

Still referring to FIG. 3H, 3D CNN 242k is trained as known in the art of the present disclosure on class of negatively interpreted medical images of prior patients (e.g., images of non-cancerous patients, images of an absence of a surgical tool within an anatomical region, etc.) to render a preliminary feature assessment 231k of the medical imaging of a body represented by volumetric medical imaging data 30b. Additionally, 3D CNN 242k is operated via a relevancy mapping by salient image manager 43 to output 3D salient image data 236k for purposes of generating a volumetric salient image illustrative of feature assessment 231k (e.g., a 3D heatmap, a 3D feature map or an activation map). Further, 3D CNN 242k is operated via GUI(s) as previously described in the present disclosure in accordance with medical imaging interaction data 34k or feature assessment interaction data 35k.

Still referring to FIG. 3H, a classifier/predictor 242l is structured to generate a final feature assessment 231l of the medical imaging of a body represented by volumetric medical imaging data 30b. In practice, classifier/predictor 242l may implement any technique as known in the art of the present disclosure for combining preliminary feature assessment 231j and preliminary feature assessment 231k to render a final feature assessment 231l. In one embodiment, classifier/predictor 242l may average risk scores associated with preliminary feature assessment 231j and preliminary feature assessment 231k to thereby render final feature assessment 231l. In a second embodiment, classifier/predictor 242l may implement a fully connected layer on behalf of networks 242j and 242k.

Still referring to FIG. 3H, classifier/predictor 242l is further structured to output salient image data 236l for purposes of generating a volumetric salient image (e.g., a 3D heatmap, a 3D feature map or an activation map). In practice, classifier/predictor 242l may implement any technique as known in the art of the present disclosure for combining filter outputs of the convolutional layers of networks 242j and 242k to produce salient image data 236l. In one embodiment, classifier/predictor 242l may average the filter outputs of the last convolutional layers of networks 242j and 242k to produce salient image data 236l.

Figure 3I:
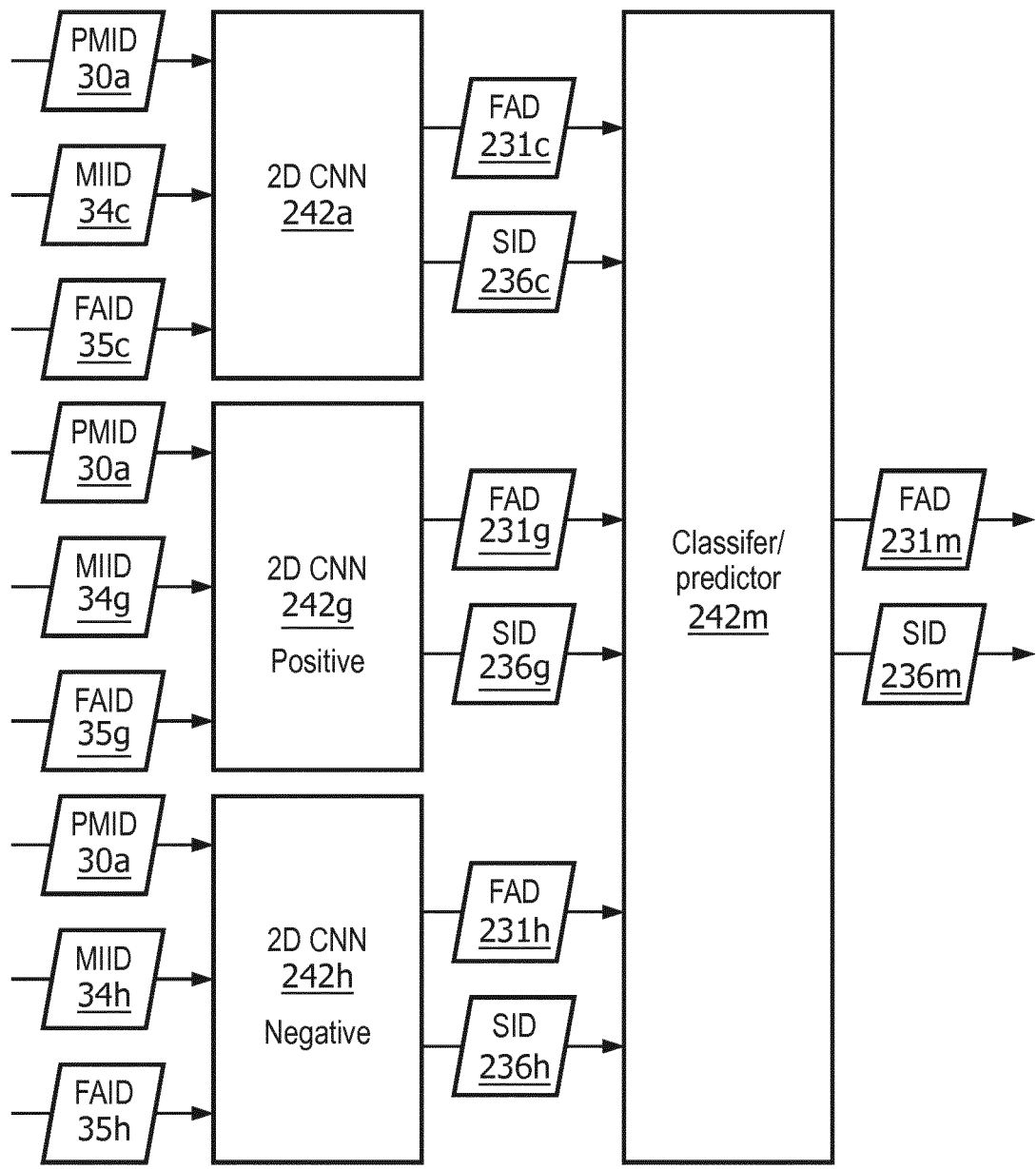
FIG. 3I illustrates a first exemplary embodiment of a parallel network of 2D CNNs in accordance with the principles of the present disclosure.

In a ninth embodiment of AI engine 40 as shown in FIG. 3I, a classifier/predictor 242m is structured to generate a final feature assessment 231m of the medical imaging of a body represented by planar medical imaging data 30a. In practice, classifier/predictor 242m may implement any technique as known in the art of the present disclosure for combining a preliminary feature assessment 231c from 2D CNN 242a (FIG. 3A), preliminary feature assessment 231g from 2D CNN 242g (FIG. 3G) and preliminary feature assessment 231h from 3D CNN 242h (FIG. 3G) to render final feature assessment 231m. In one embodiment, classifier/predictor 242m may average risk scores associated with preliminary feature assessment 231c, preliminary feature assessment 231g and preliminary feature assessment 231h to thereby render final feature assessment 231m. In a second embodiment, classifier/predictor 242m may implement a fully connected layer on behalf of networks 242a, 242g and 242h.

Still referring to FIG. 3I, classifier/predictor 241m is further structured to output salient image data 236m for purposes of generating a planar salient image illustrative of feature assessment 231m (e.g., a 2D heatmap, a 2D feature map or an activation map). In practice, classifier/predictor 241m may implement any technique as known in the art of the present disclosure for combining filter outputs of the convolutional layers of networks 242c, 242g and 242h to produce salient image data 236m. In one embodiment, classifier/predictor 242i may average the filter outputs of the last convolutional layers of networks 242c, 242g and 242h to produce salient image data 236m.

Figure 3J:
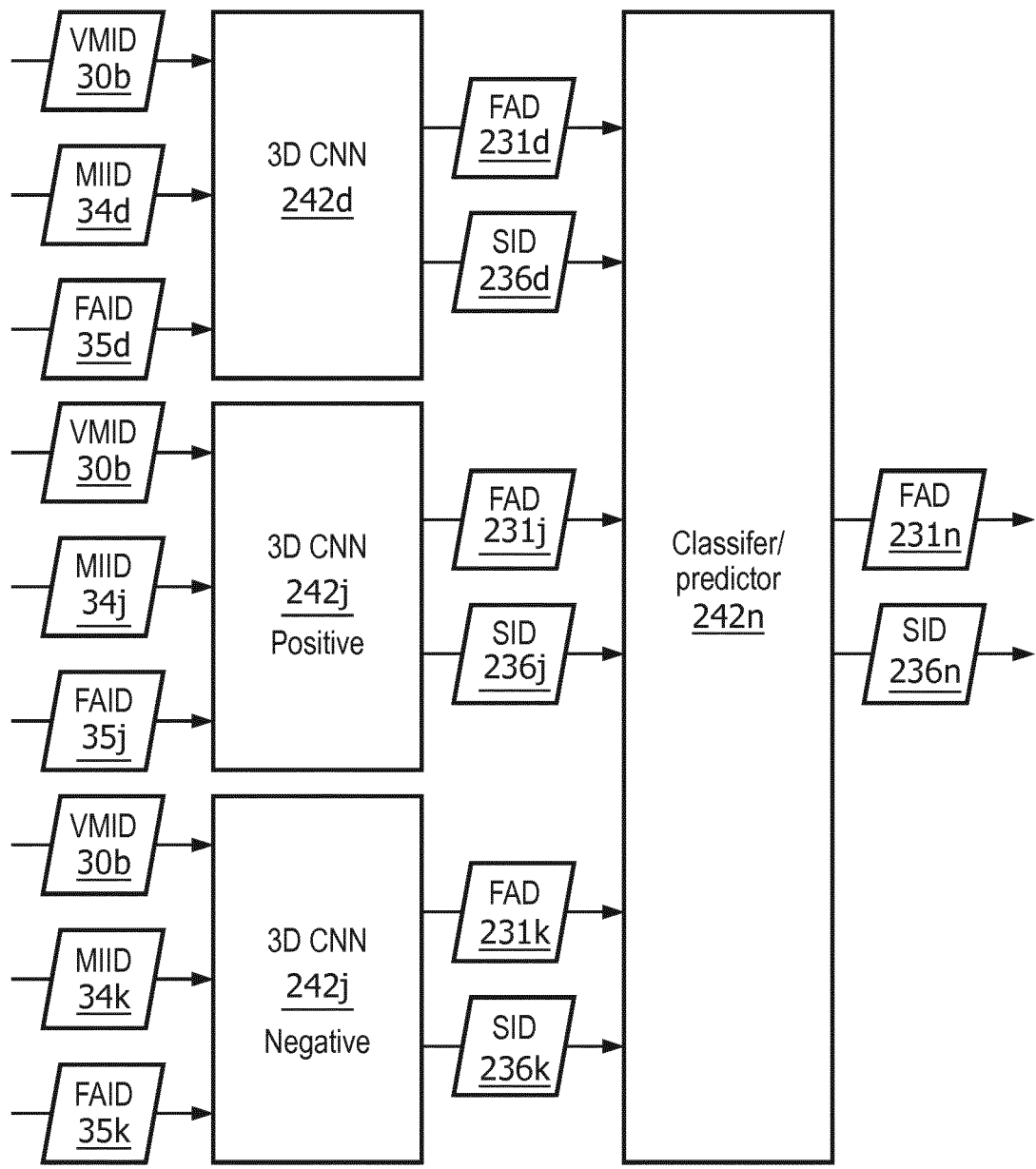
FIG. 3J illustrates a first exemplary embodiment of a parallel network of 3D CNNs in accordance with the principles of the present disclosure.

In a tenth embodiment of AI engine 40 as shown in FIG. 3J, a classifier/predictor 242n is structured to generate a final feature assessment 231n of the medical imaging of a body represented by volumetric medical imaging data 30b. In practice, classifier/predictor 242n may implement any technique as known in the art of the present disclosure for combining a preliminary feature assessment 231c from 3D CNN 242a (FIG. 3A), preliminary feature assessment 231j from 3D CNN 242J (FIG. 3H) and preliminary feature assessment 231K from 3D CNN 242k (FIG. 3h) to render final feature assessment 231N. In one embodiment, classifier/predictor 242n may average risk scores associated with preliminary feature assessment 231c, preliminary feature assessment 231j and preliminary feature assessment 231k to thereby render final feature assessment 231n. In a second embodiment, classifier/predictor 242mn may implement a fully connected layer on behalf of networks 242c, 242j and 242k.

Still referring to FIG. 3J, classifier/predictor 242n is further structured to output salient image data 236n for purposes of generating a volumetric salient image illustrative of feature assessment 231n (e.g., a 3D heatmap, a 3D feature map or an activation map). In practice, classifier/ predictor 242n may implement any technique as known in the art of the present disclosure for combining filter outputs of the convolutional layers of networks 242c, 242j and 242k to produce salient image data 236n. In one embodiment, classifier/predictor 242n may average the filter outputs of the last convolutional layers of networks 242c, 242j and 242k to produce salient image data 236n.

Referring back to FIG. 2A, medical image display engine 50 controls a display of medical image(s) 32 and salient image(s) 33 as previously described for stage S24 of FIG. 1. To this end, medical image display engine 50 includes an image viewer 51, a medical image generator 52, and a salient image generator 53 for implementation of a salient visualization method represented by a flowchart 150 of FIG. 2C.

Referring to both FIGS. 2A and 2C, during a stage S152 of flowchart 150, planar medical imaging data 30a or volumetric medical imaging data 40a may be received by medical image display engine 50 in viewable form. Subsequent to such receipt, autonomously or via clinician activation, image viewer 51 proceeds to implement a display of medical images represented by planar medical imaging data 30a or volumetric medical imaging data 40a, and further provide an image navigation function (e.g., zoom in, zoom out, rotation, etc.) and an image annotation function for a clinician viewing the displayed medical images. Additionally, medical image generator 52 may, autonomously or via clinician activation, implement (1) a volume rendering of a series of planar medical images represented by planar medical imaging data 30, (2) an image segmentation of a volumetric medical image represented by volumetric medical imaging data 40 or by a volume rendering, or (3) any other techniques known in the art for generating additional medical images.

During stage S152, planar medical imaging data 30a or volumetric medical imaging data 40a may alternatively be received by medical image display engine 50 in raw form. Subsequent to such receipt, medical image generator 51 may implement an image reconstruction technique of planar medical imaging data 30a or volumetric medical imaging data 30b. Subsequent to such imaging reconstruction, autonomously or via clinician activation, image viewer 51 proceeds to implement a display of the reconstructed medical images, and further provide an image navigation function (e.g., zoom in, zoom out, rotate, etc.) and an image annotation function for a clinician viewing the displayed reconstructed medical images. Additionally, medical image generator 52 may, autonomously or via clinician activation, implement (1) a volume rendering of a series of reconstructed planar medical images, (2) an image segmentation of a volumetric medical image represented by a reconstructed volumetric medical image or by a volume rendering, or (3) any other techniques known in the art for generating additional medical images.

Subsequently or concurrently with stage S152, during a stage S154 of flowchart feature assessment data 31a and salient image data 36a are received by medical image display engine 50. Subsequent to such receipt, autonomously or via clinician activation, image viewer 51 proceeds to display the feature assessment data 31a in a textual format or a graphical format, and salient image generator 53 process salient image data 36a to generate salient image(s) 33 for display by image viewer 51.

Again in practice, salient image data 36a is representative of the relevance of each feature of masked/revised medical imaging data 30a/30b to the new feature assessment 31a. In one embodiment for any type of machine learning model, salient image data 36a provides a scaling of each pixel represented by planar medical imaging data 30a and each voxel of volumetric medical imaging data 40a from least relevant pixel(s)/voxel(s) (e.g., 0) to most relevant pixel(s)/voxel(s) (e.g., 169). The scaling enables salient image generator 51 to generate a heatmap or a feature map. In a second embodiment particularly for neural networks, scaling image data 36a provides filter outputs ranging from least relevant filter output(s) to most relevant filter output(s).

In one convolutional neural network embodiment, salient image manager 43 calculates a gradient of a class with respective to the last 3D convolutional layer of the CNN and get the weights of each filter output using global average pooling whereby salient image generator 53 generated a heatmap by applying the weights to corresponding filter output, and ReLU, and then normalizes and scales the filter outputs to a desired size.

Figure 4A:
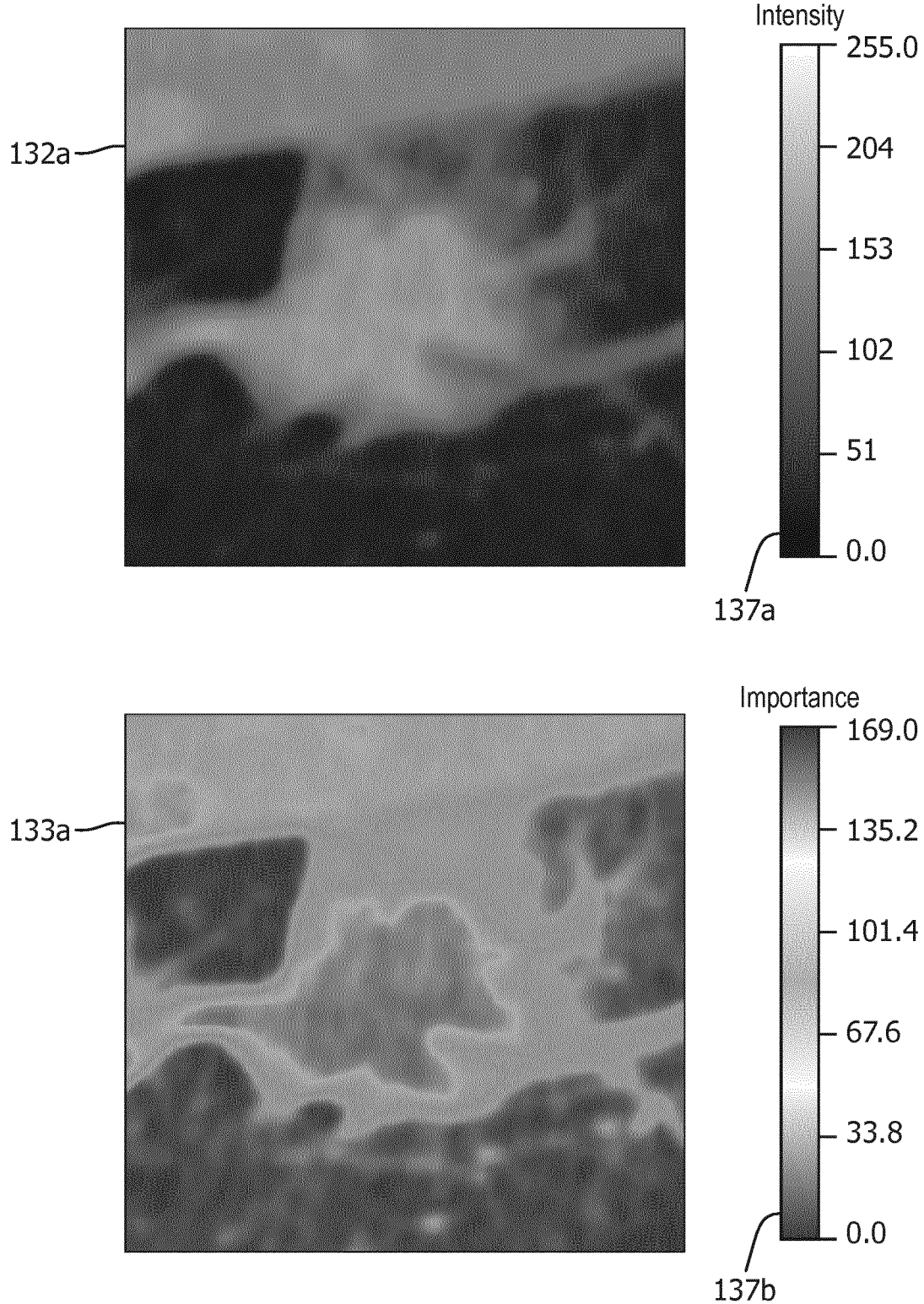
FIG. 4A illustrates an exemplary 2D planar CT image and an exemplary generation of a 2D planar heatmap corresponding to the 2D planar CT image as known in the art of the present disclosure.

For example, FIG. 4A shows an exemplary planar CT image 132a with associated intensity scale 137a ranging from 0 to 255, and a corresponding planar heatmap 133a with associated importance scale 137b ranging from 0 to 169. For FIG. 4A, each pixel of planar CT image 132a has been assigned an intensity valve based on relevancy level to the feature assessment 31a, and an importance level of pixel as displayed in planar heatmap 133a signifies the relevancy level of the pixel to feature assessment 31a, such as, for example, a pixel shown at level of 0 within planar heatmap 133a signifies this pixel has a least relevancy level to feature assessment 31a and a pixel shown at level of 169 within planar heatmap 133a signifies this pixel has a most relevancy level to feature assessment 31a.

Figure 4B:
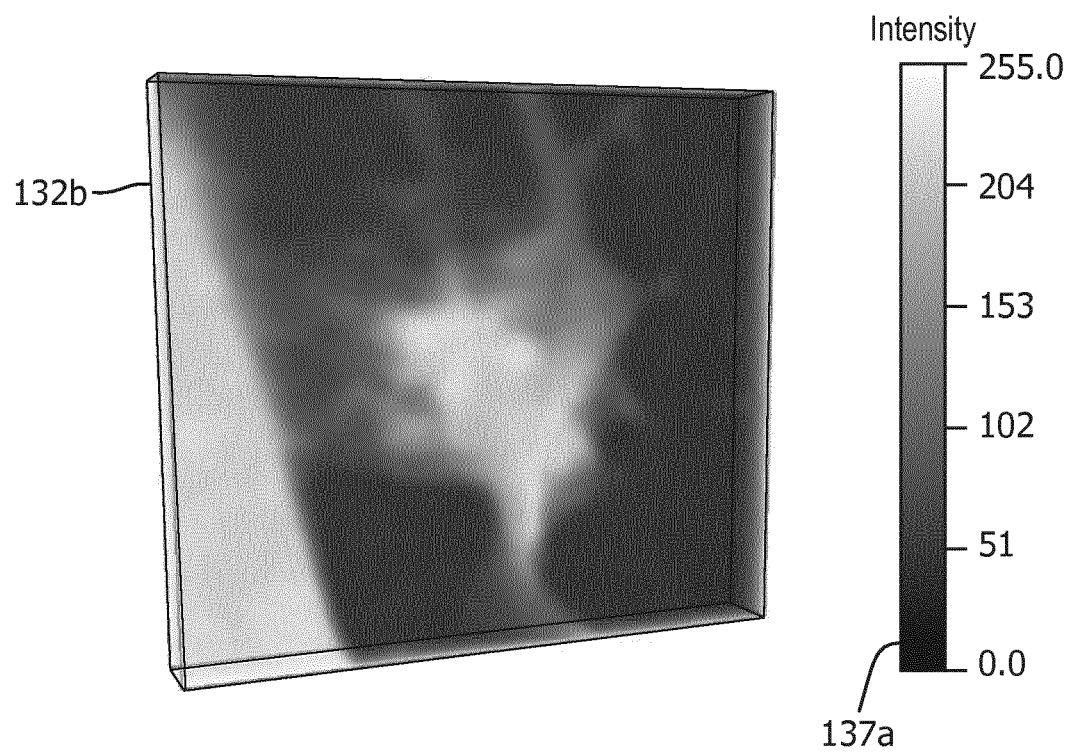
FIG. 4B illustrates an exemplary rendering of a 3D volumetric CT image and an exemplary generation of 3D volumetric heatmap corresponding to the 3D volumetric CT image in accordance with the principles of the present disclosure.
Figure 4B:
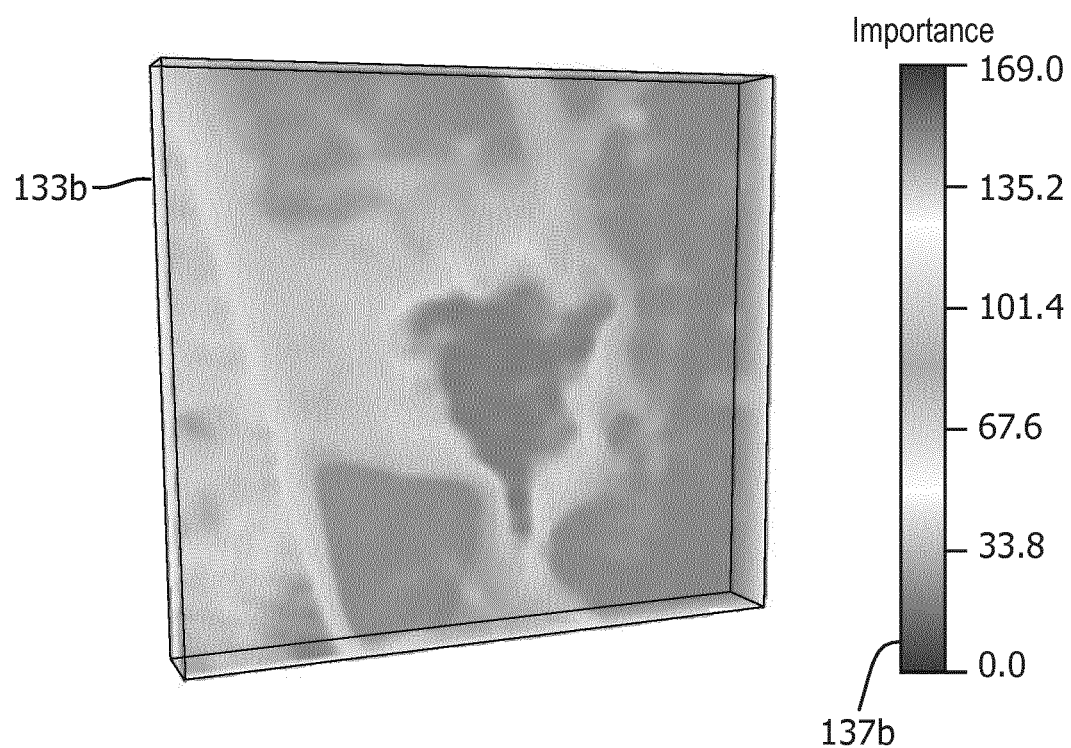

Similarly for example, FIG. 4B shows an exemplary volumetric CT image 132b with associated intensity scale 137a ranging from 0 to 255, and a corresponding volumetric heatmap 133b with associated importance scale 137b ranging from 0 to 169. For FIG. 4A, each voxel of volumetric CT image 132b has been assigned an intensity valve based on relevancy level to the feature assessment 31a, and an importance level of voxel as displayed in volumetric heatmap 133b signifies the relevancy level of the pixel to feature assessment 31a, such as, for example, a voxel shown at level of 0 within volumetric heatmap 133b signifies this voxel has a least relevancy level to feature assessment 31a and a voxel shown at level of 169 within volumetric heatmap 133b signifies this voxel has a most relevancy level to feature assessment 31a.

Referring back to FIG. 2C, for heatmap embodiments, stage S154 further encompasses salient image generator 53 (FIG. 2A) defining reslicing salient planes intersecting with a volumetric heatmap to expose the most relevant or descriptive information for feature assessment 31a of the medical imaging 30, and image viewer 51 providing user interaction functions for a manual exploration and navigation by a clinician within the volumetric space of the medical imaging 30 in view of a relevance based guidance.

More particularly, salient image generator 53 executes, autonomously or via a clinician activation, (1) a relevancy reslicing of a planar salient image from the volumetric salient image based on a relevancy level of each feature to a feature assessment 31 of the volumetric medical image by the machine learning model(s), or (2) a user specified reslicing of a center point or an orientation of a planar salient image from the volumetric salient image.

In practice, a relevancy reslicing and a user specified reslicing of stage S154 are premised on a salient voxel of a volumetric salient image has a relevancy level exceeding a relevancy threshold and a plurality of salient voxels will define a salient view of the assessed features of volumetric medical imaging data 30b. For reslicing purposes, a center point and an orientation of the resliced planar salient image within the volumetric salient image is derived from an intersection of a resliced salient plane with the volumetric salient image that includes one or more salient voxels.

In practice a relevancy reslicing involves an identification of salient voxels, a delineating of plane intersections including one or more salient voxels and then a selection of a one of the plane intersections optimizing a view of salient voxels, such as, for example, a selection of having a highest spatial distribution salient voxels, a highest summation of salient voxels, or a highest average of salient voxels.

In practice a user specified reslicing involves an identification of salient voxels, a user specification of a center point or an orientation of a plane intersection, a delineating of plane intersections including one or more salient voxels and then a selection of a one of the plane intersections optimizing a view of salient voxels, such as, for example, a selection of having a highest spatial distribution salient voxels, a highest summation of salient voxels, or a highest average of salient voxels.

Figure 5A:
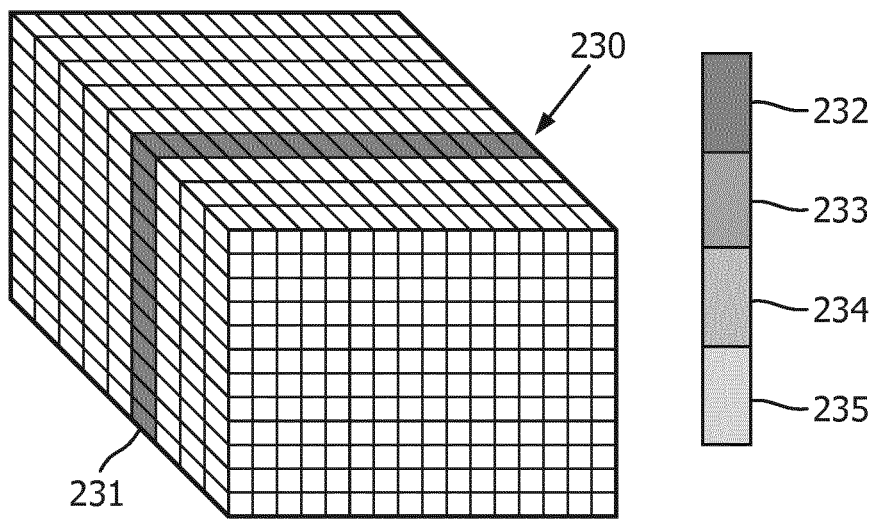
FIGS. 5A-5F illustrate an exemplary reslicing of a 3D volumetric salient image at a first principle plane in accordance with the principles of the present disclosure.

For example, as simplicity shown in FIG. 5A for clarity reasons, a volumetric salient image 230 includes a set 231 of rows of salient voxels having relevancy level 232-235 of increasing intensity with each relevancy level exceeding a relevancy threshold. For this example, the relevancy threshold may be 200, relevancy level 232 may 210, relevancy level 233 may 225, relevancy level 234 may be 240 and relevancy level 235 may be 255.

Figure 5B:
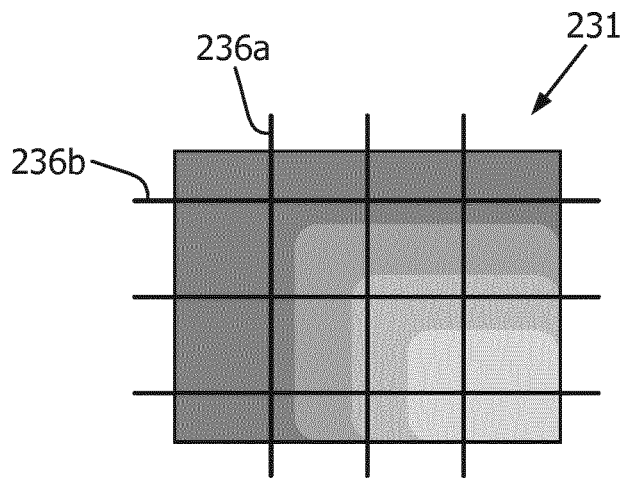

FIG. 5B illustrates a XY planar view of rows 231 of salient voxels with the horizontal lines representing intersections of candidate reslice salient YZ planes with the volumetric salient image 230 that includes one or more salient voxels and the vertical line representing intersections of candidate reslice salient XZ planes with the volumetric salient image 230 that includes one or more salient voxels. For FIG. 5B, reslice salient plane 236a or reslice salient plane 236b may be chosen in view of a highest spatial distribution salient voxels, a highest summation of salient voxels, or a highest average of salient voxels.

Figure 5C:
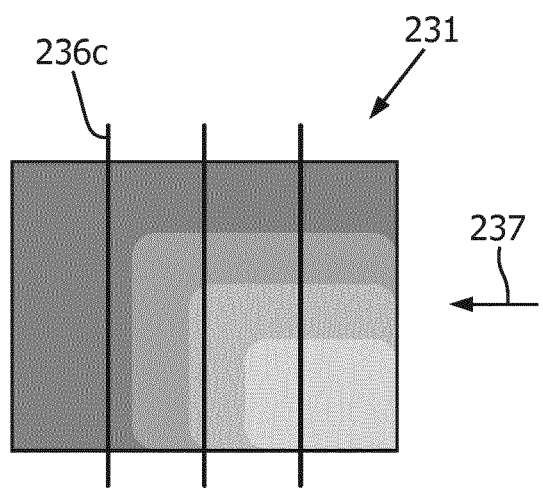

FIG. 5C illustrates a XY planar view of rows 231 of salient voxels with the horizontal represent intersections of candidate reslice salient YZ planes with the volumetric salient image 230 that includes one or more salient voxels. For FIG. 5C, reslice salient plane 236c may be chosen in view of a highest spatial distribution salient voxels, a highest summation of salient voxels, or a highest average of salient voxels.

Figure 5D:
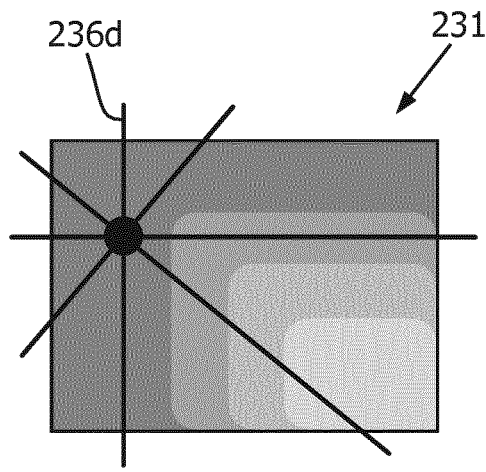

FIG. 5D illustrates a XY planar view of rows 231 of salient voxels with the black dot representing a centroid of the salient voxels and the lines represent intersections of candidate reslice salient YZ planes with the volumetric salient image 230 through the centroid that includes one or more salient voxels. For FIG. 5D, reslice salient plane 236d may be chosen in view of a highest spatial distribution salient voxels, a highest summation of salient voxels, or a highest average of salient voxels relative to the centroid.

In practice, the centroid may be calculated as an arithmetic mean of all the 3D points ($p \in R^3$) of the salient voxels.

Figure 5E:
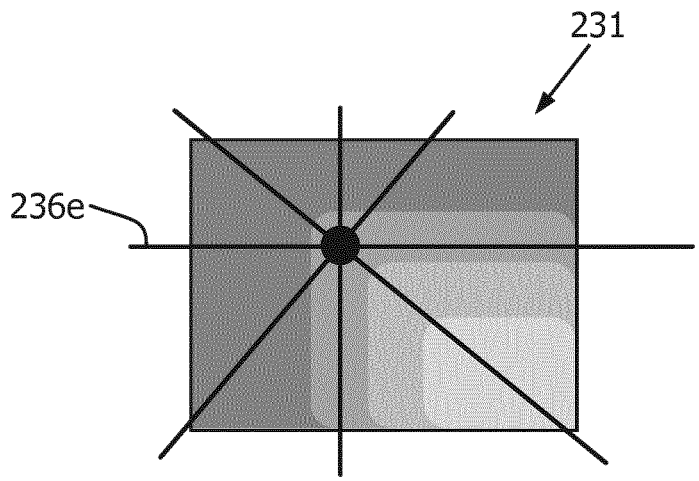

FIG. 5E illustrates a XY planar view of rows 231 of salient voxels with the black dot representing user specified center point and the lines represent intersections of candidate reslice salient YZ planes with the volumetric salient image 230 through the user specified location that includes one or more salient voxels. For FIG. 5E, reslice salient plane 236e may be chosen in view of a highest spatial distribution salient voxels, a highest summation of salient voxels, or a highest average of salient voxels relative to the user specified center point.

Figure 5F:
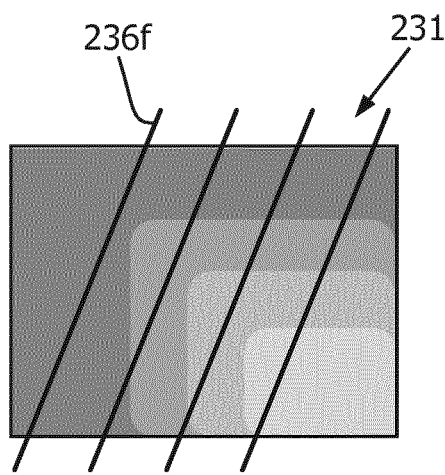

FIG. 5F illustrates a XY planar view of rows 231 of salient voxels with the black lines representing intersections of candidate reslice salient YZ planes with the volumetric salient image 230 at a user specified orientation that includes one or more salient voxels. For FIG. 5F, reslice salient plane 236F may be chosen in view of a highest spatial distribution salient voxels, a highest summation of salient voxels, or a highest average of salient voxels relative to the user specified center point.

Figure 6A:
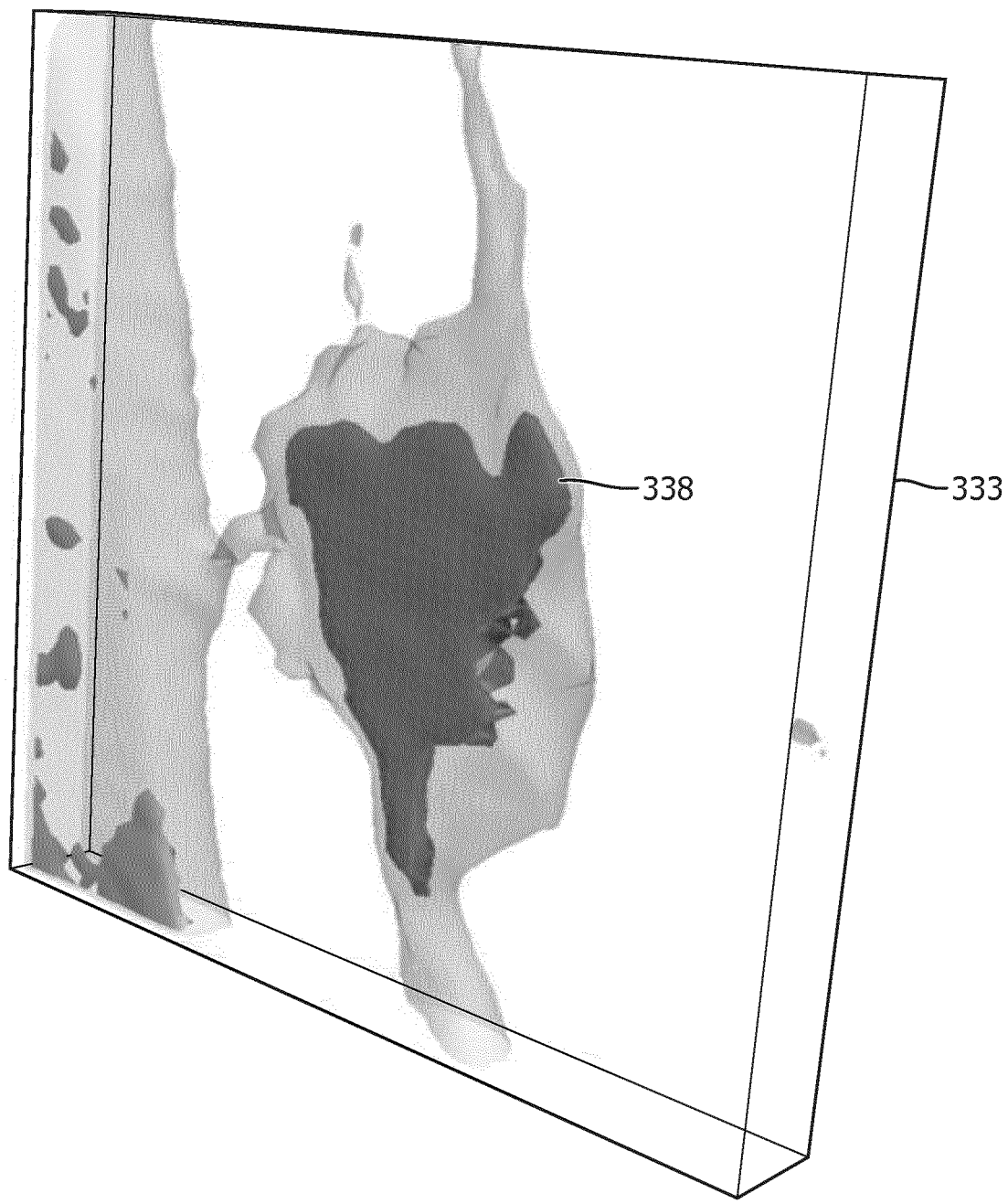
FIG. 6A illustrates an exemplary feature segmentation in accordance with the principles of the present disclosure.
Figure 6B:
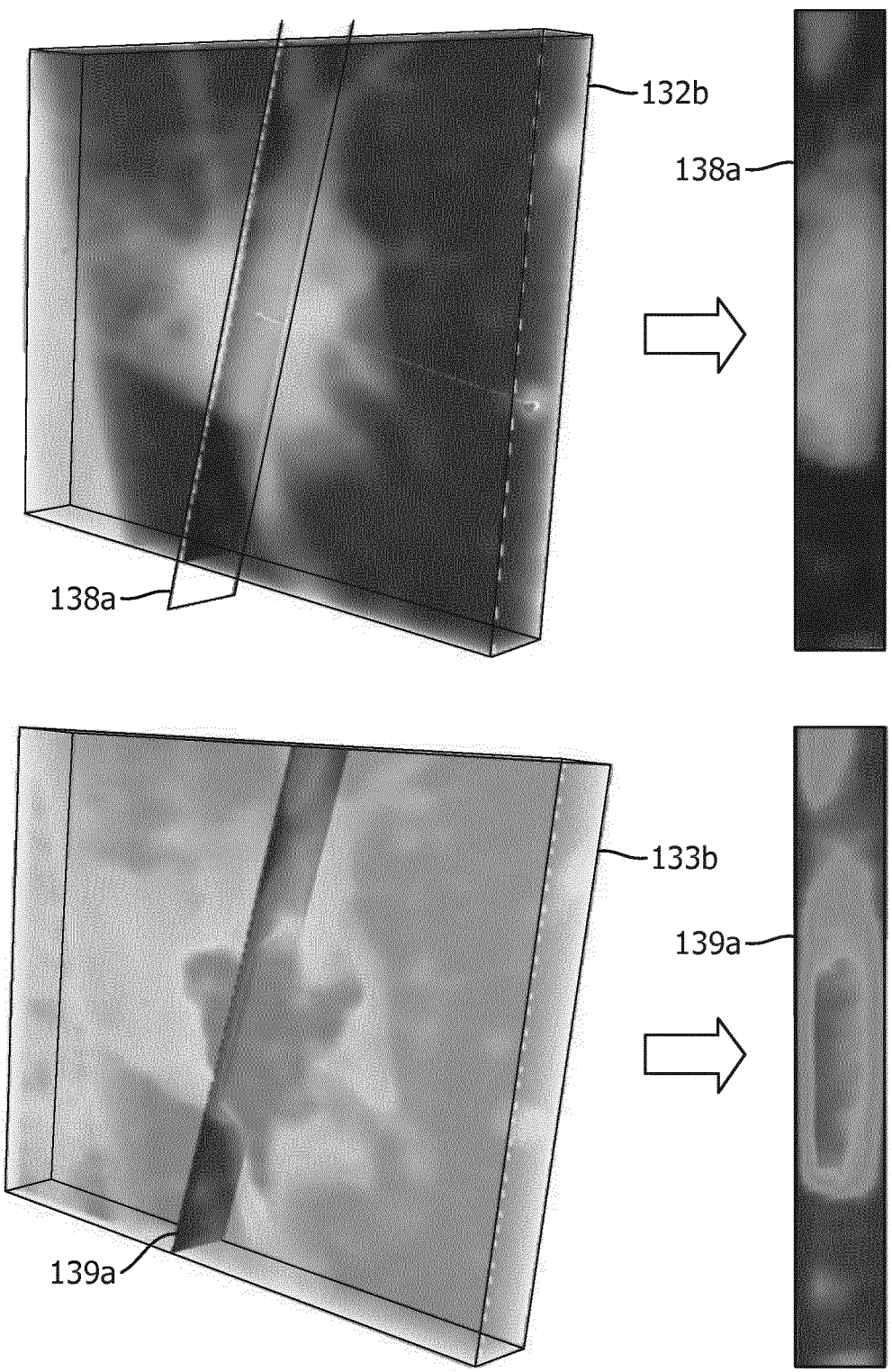
FIG. 6B illustrates an exemplary reslicing of the 3D volumetric CT image and the 3D volumetric heatmap of FIG. 4B at a first principle plane in accordance with the principles of the present disclosure.
Figure 6C:
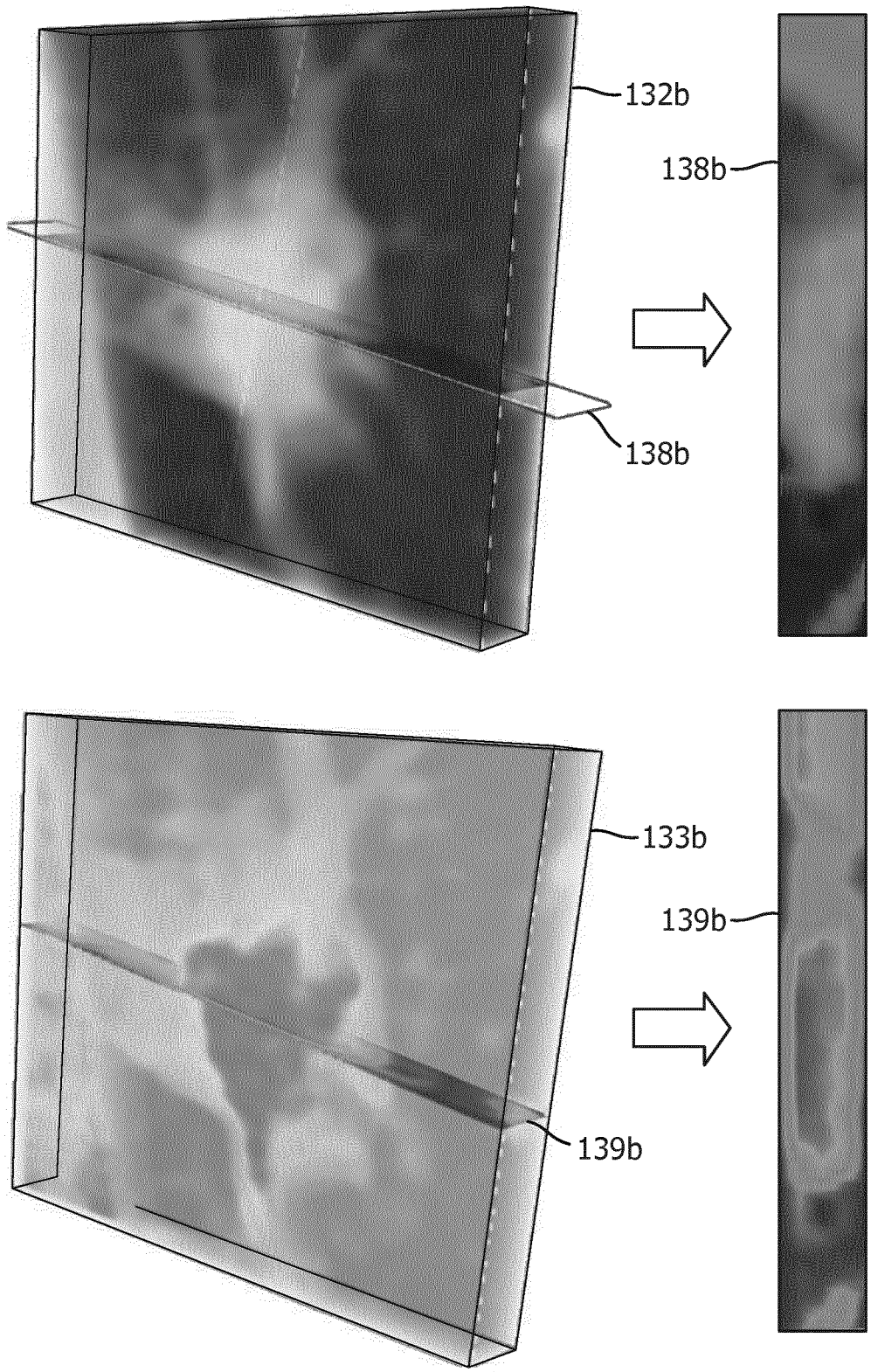
FIG. 6C illustrates an exemplary reslicing of the 3D volumetric CT image and the 3D volumetric heatmap of FIG. 4B at a second principle plane in accordance with the principles of the present disclosure.
Figure 6D:
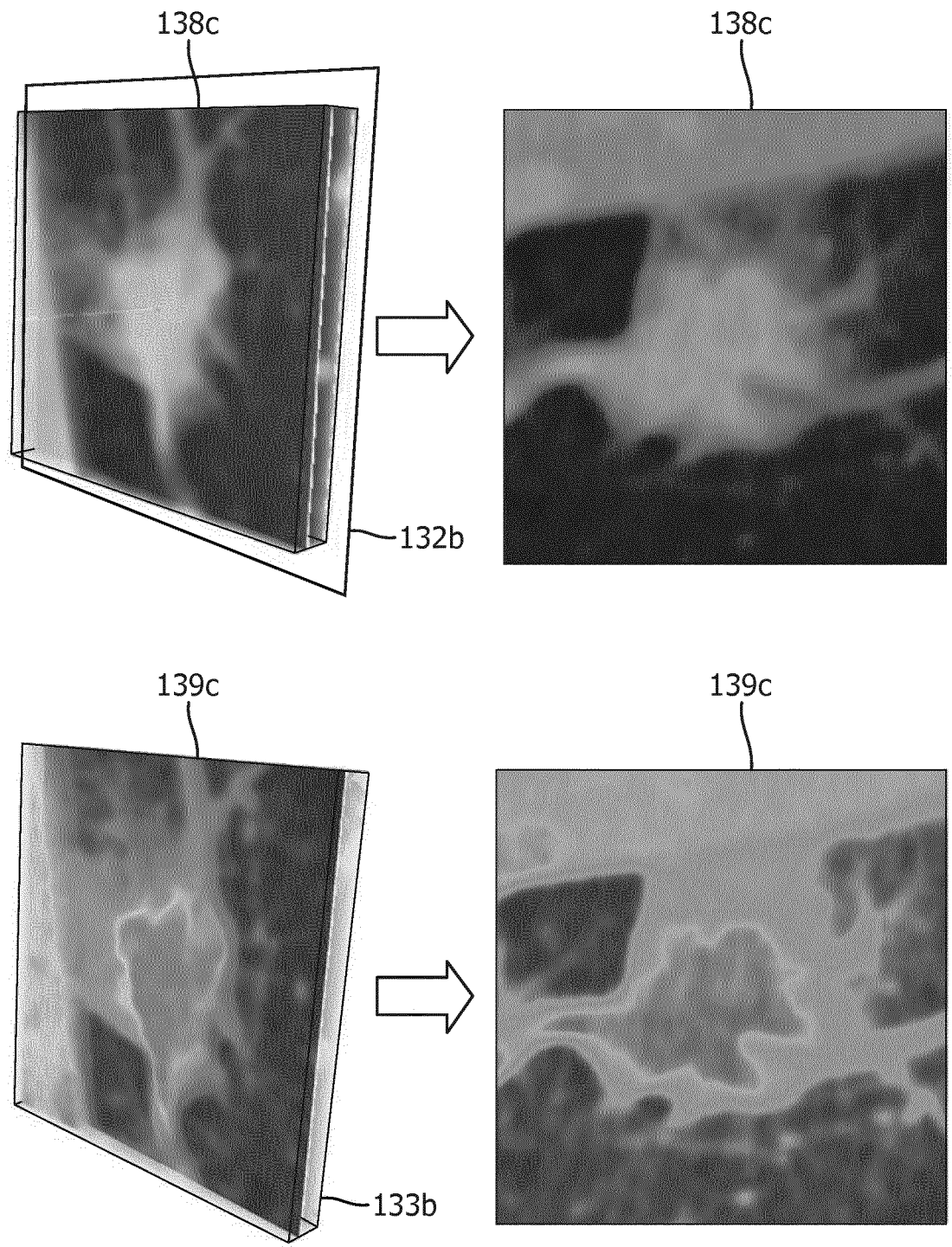
FIG. 6D illustrates an exemplary reslicing of the 3D volumetric CT image and the 3D volumetric heatmap of FIG. 4B at a third principle plane in accordance with the principles of the present disclosure.

Referring back to FIGS. 2A and 2C, during stage S154, image viewer 51 may for example control a display of:
(1) 3D volume renderings of reconstructed medical image 132a and a corresponding salient visual volume image (e.g., 3D volumetric CT image 133b with associated intensity scale 137l and of a corresponding 3D salient visual image 137b with associated relevancy scale 234 as shown in FIG. 4B);
(2) a feature segmentation 338 from a medical image 132a as shown in FIG. 6A;
(3) an intelligent reslicing at of reconstructed medical image 132a and a corresponding salient visual volume image following oblique planes (e.g., a reslicing 138a of 3D volumetric CT image 132b and a reslicing 139a of 3D salient visual image 133b at a first principle plane as shown in FIG. 6B, a reslicing 138b of 3D volumetric CT image 132a and a reslicing 139b of 3D salient visual image 133b at a second principle plane as shown in FIG. 6C, and a reslicing 138c of 3D volumetric CT image 132a and a reslicing 139c of 3D salient visual image 133b at a third principle plane as shown in FIG. 6D);
(4) an intelligent reslicing in standard orthogonal planes (not shown) (e.g., a sagittal plane, a coronal plane and an axial plane); and/or
(5) a manual reslicing reconstructed medical image and corresponding salient visual volume image as defined by the user via a user input device (e.g., a touch screen, a mouse, a keyboard, augmented reality glasses, etc.).

More particularly, volume rendering is calculated using methods known in art of the present disclosure, such as, for example, ray casting algorithm and shown in comparison to the input image. A comparison to input image may be achieved using side-by-side visualization or image blending. Importance map may be resampled to the size of the input image using common interpolation techniques known in the art of the present disclosure, such as, for example, a linear-based interpolation or a spline-based interpolation.

Reslicing plane orientation and position may be defined manually by the user via GUI or automatically by salient image generator 53. In one embodiment, salient mage generator 53 may position reslicing plane in one of the standard axial, sagittal, and coronal views or according to principal planes along highest variance (spread) in one of the most prominent salient features in the importance map (e.g., a salient feature 338 of 3D volumetric CT image 333 as shown in FIG. 6A). These most important salient feature(s) may be extracted by salient mage generator 53 from the reconstructed medical image 132a in order to make the feature assessment. Principal planes are defined by the center point and normal. Center point is located at the centroid calculated from the locations of the most important salient feature(s) within the heatmap 133b (FIG. 4B). In practice, the centroid may be calculated as an arithmetic mean of all the 3D points ($p \in R^3$) of the salient voxels. Normal vectors to principal planes are defined by three eigenvectors with the largest eigenvalue that was calculated on the most important salient features using principal component analysis (PCA) method known in art of the present disclosure. All reslicing planes may be either shown in a 3D context or as a 2D image, as well as compared to 3D volumetric CT image 132a that is also resliced at the same orientation.

More particularly to FIGS. 6A-6D, voxels of salient feature 338 of 3D volumetric CT image 132a as shown in FIG. 6A is automatically extracted by medical imaging display engine 50 as one of the features with the highest values in the importance map that were prioritized by a 3D artificial intelligence engine in the decision-making process. Voxels of salient feature 338 is automatically extracted from the importance map using segmentation methods known in the art of the present disclosure, such as, for example, an instance intensity-based thresholding or a model-based segmentation.

FIG. 6B illustrates a reslicing 138a of 3D volumetric CT image 132a and a reslicing 139a of 3D salient visual image 133b at a first principle plane that is defined by a center point and a normal to salient feature 338 (FIG. 6A).

FIG. 6C illustrates a reslicing 138b of 3D volumetric CT image 132a and a reslicing 139b of 3D salient visual image 133b at a second principle plane that is defined by a center point and a normal to salient feature 338.

FIG. 6D illustrates a reslicing 138c of 3D volumetric CT image 132a and a reslicing 139c of 3D salient visual image 133b at a third principle plane to salient feature 338.

The center point of the reslicings 139a-139c are located at a centroid calculated from the location of salient feature 338 within 3D salient visual image 133b. Normal to the first principle plane is defined by an eigenvector with the second highest eigenvalue that was calculated from the salient feature 338 using Principal Component Analysis method that is known in art of the present disclosure. Normal to the second principle plane is defined by an eigenvector with the highest eigenvalue that was calculated from the salient feature 338 using Principal Component Analysis method that is known in art of the present disclosure. Normal to the third principle plane is defined by an eigenvector with the lowest eigenvalue that was calculated from the salient feature 338 using Principal Component Analysis method that is known in art of the present disclosure.

In practice, a user may modify the position of the first principle plane, the second principle plane and the third principle plane (e.g., move the center point along its normal via a GUI).

Figure 7:
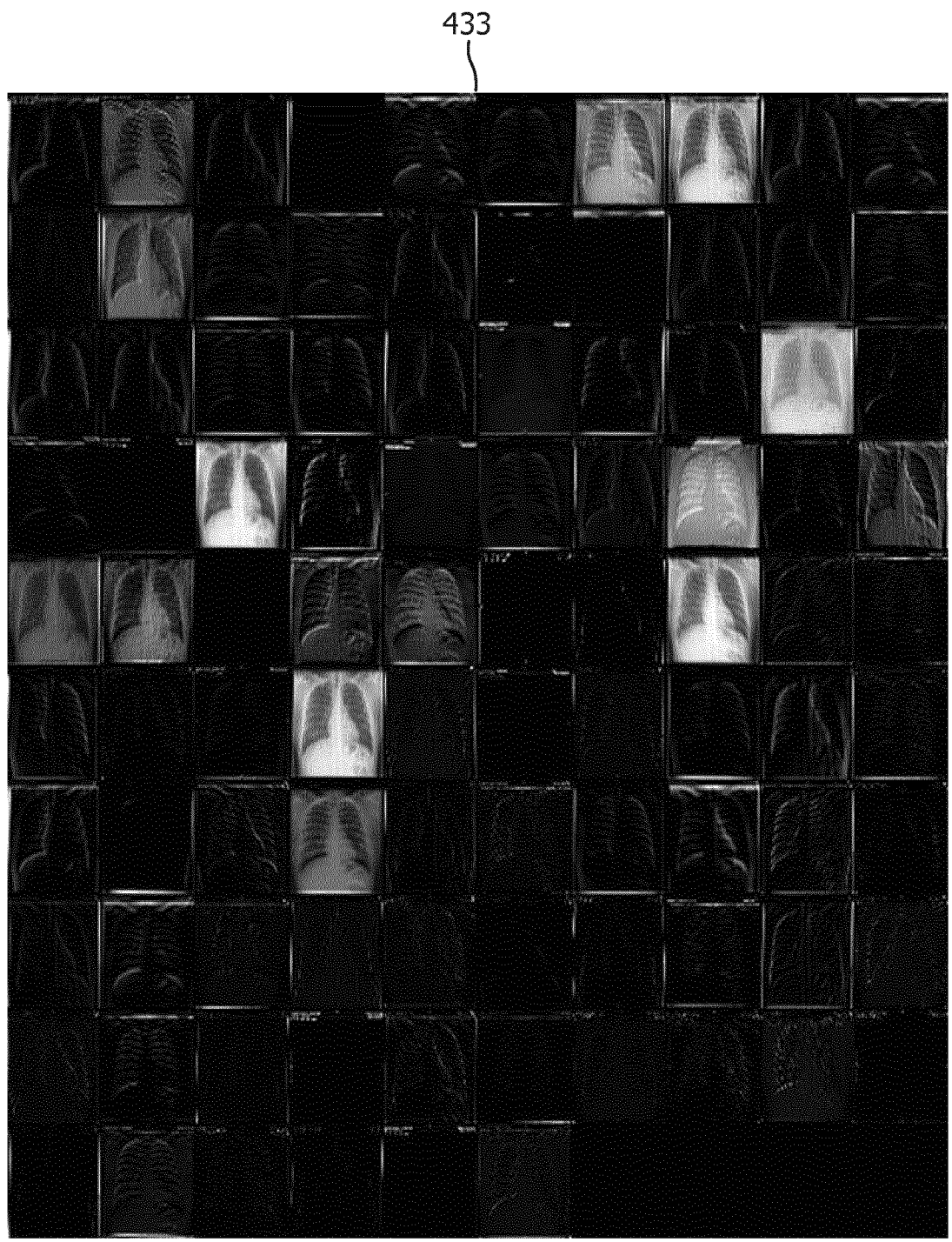
FIG. 7 illustrates an exemplary embodiment of an activation diagram in accordance with the principles of the present disclosure.

Further in practice, salient image generator 53 may control a display of an activation diagram derived from feature elements assessed by AI engine 40. For example, salient image generator 53 may display each individual filter output in an activation diagram 433 of activation maps as shown in FIG. 7. By choosing a threshold of total weights (e.g., 90%), the activation maps are ranked by the top n activations associated with those top weights to thereby list the activation maps in descending order. This embodiment is particularly useful, for a new clinician is in early career, or medical students who are not very experience, and can be a good reference in addition to the textbook.

Figure 8:
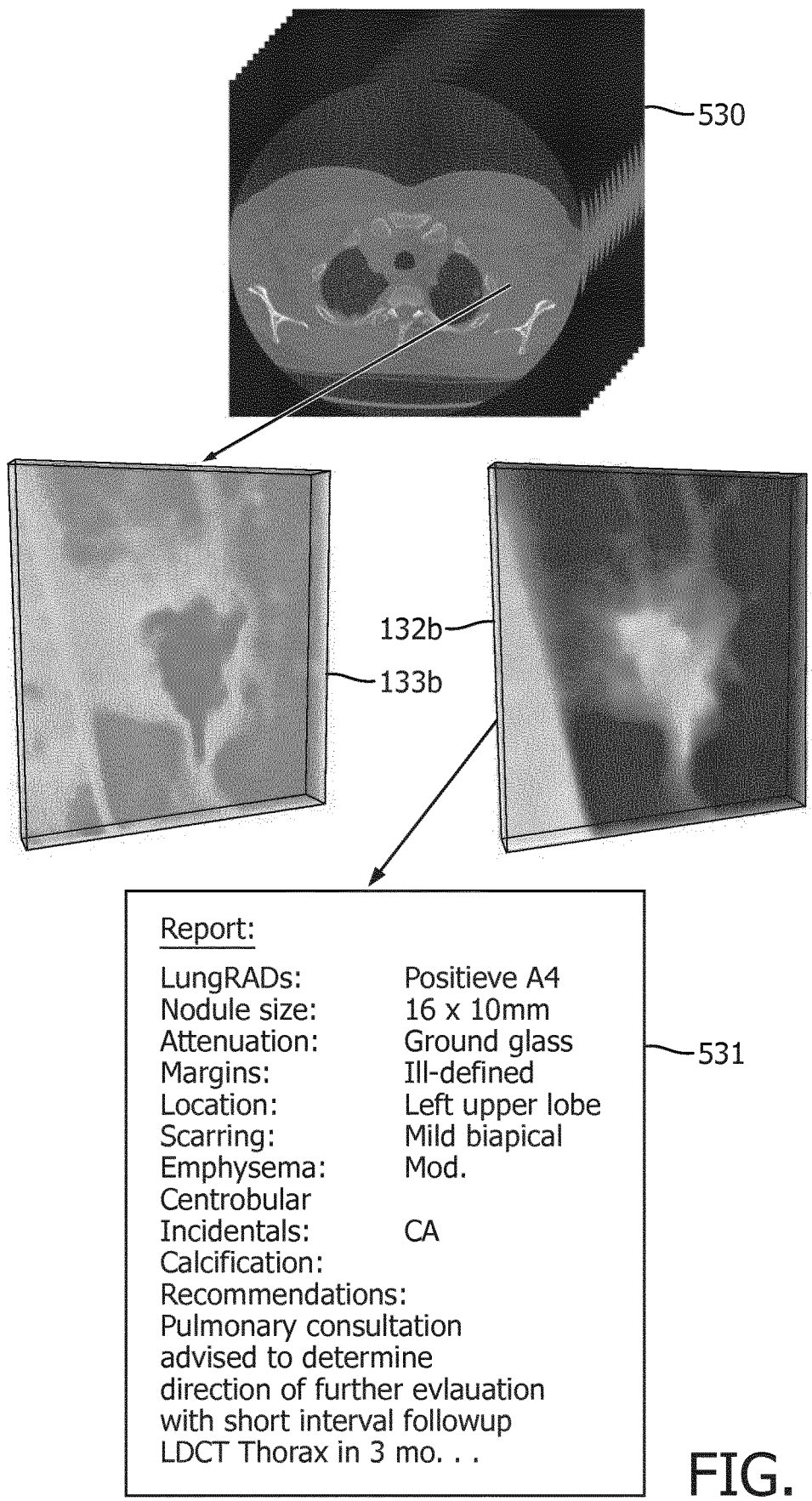
FIG. 8 illustrates an exemplary embodiment of clinical reporting in accordance with the principles of the present disclosure.

Additionally in practice, 3D salient visual image provides richer information on contours than 2D salient visual image. For example, from a 3D heatmap, user-specified grayscale pixel value visualizes a contour of an area of interest (e.g., a nodule) whereby the contour may be translated to clinical information that otherwise requires human annotation (e.g., an area of interest volume, largest radius, the axis direction of the largest radius, the texture of the contour, etc.) and then generate text output. For example, as shown in FIG. 8, clinician reporting aspect of the present disclosure provides for automatically linking of generated text information 531 to images 30a, 133b and 132b.

Figure 9A:
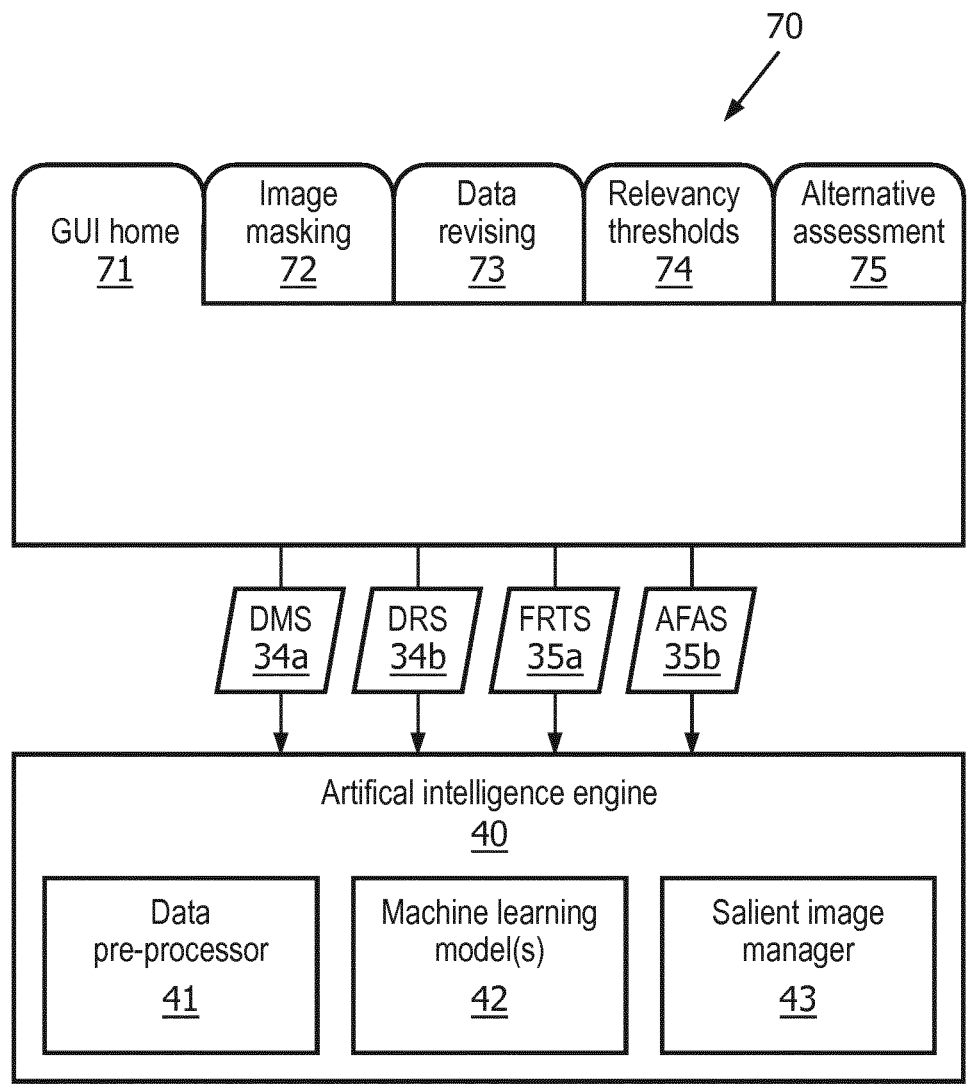
FIG. 9A illustrates exemplary embodiment of a graphical user interface in accordance with the principles of the present disclosure.
Figure 9B:
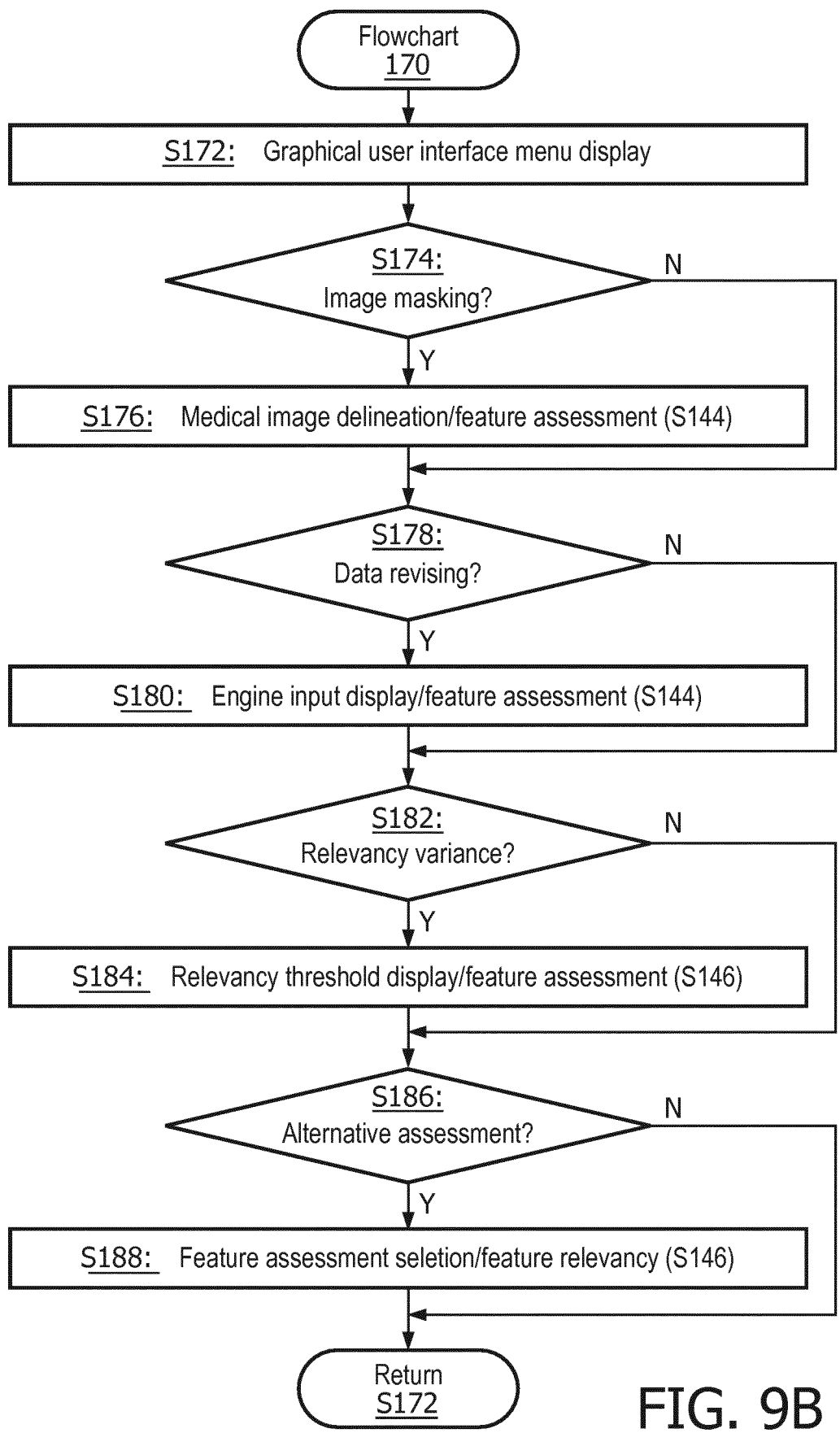
FIG. 9B illustrates a saline manipulation method in accordance with the principles of the present disclosure.

To facilitate a further understanding of the present disclosure, the following description of FIGS. 9A and 9B teach various embodiments of a graphical user interface of the present disclosure. From the description of FIGS. 9A and 9B, those having ordinary skill in the art of the present disclosure will appreciate how to apply the present disclosure for making and using numerous and various additional embodiments of graphical user interface of the present disclosure.

Referring to FIGS. 2A and 2B, a graphical user interface 70 employs a GUI home tab 71, an image masking tab 72, a data revising tab 73, a relevancy threshold tab 74 and an alternative assessment tab 75 for executing a flowchart 170 as an implementation of salient manipulation stage S26 as previously described in connection with FIG. 1.

To this end, a stage S172 of flowchart 170 encompasses an activation of GUI 70 for GUI 70 to thereby received user input data via a user input device (e.g., a mouse, a keyboard, a touchscreen, augmented reality glasses, etc.) and optionally auxiliary patient information (e.g., patient age, medical history, etc.). From the inputs, GUI 70 processes through states S174-S188 of flowchart 170 to thereby interact with AI engine 40 as user specified to manipulate a salient visualization of the feature assessment 31 of medical imaging 30.

Specifically, during a stage S174 of flowchart 170, GUI 70 ascertains if the input data is data masking data 34a received via image masking tab 72 whereby a clinician interacts with a planar medical image or a volumetric medical image directly and see how the artificial intelligence engine 40 responds. For example, the clinician may analysis salient image(s) 33 (FIG. 1) to ascertain if one or more particular area(s) of a planar medical image or a volumetric medical image is(are) irrelevant to a current feature assessment 31 (FIG. 1). If the clinician suspects one or more particular area(s) of the planar medical image or the volumetric medical image is(are) irrelevant to a current feature assessment 31 of such image, then the clinician may mask the irrelevant area(s) and view the salient image(s) to see the impact such masking has on the feature assessment 31 of medical imaging 30.

Figure 10A:
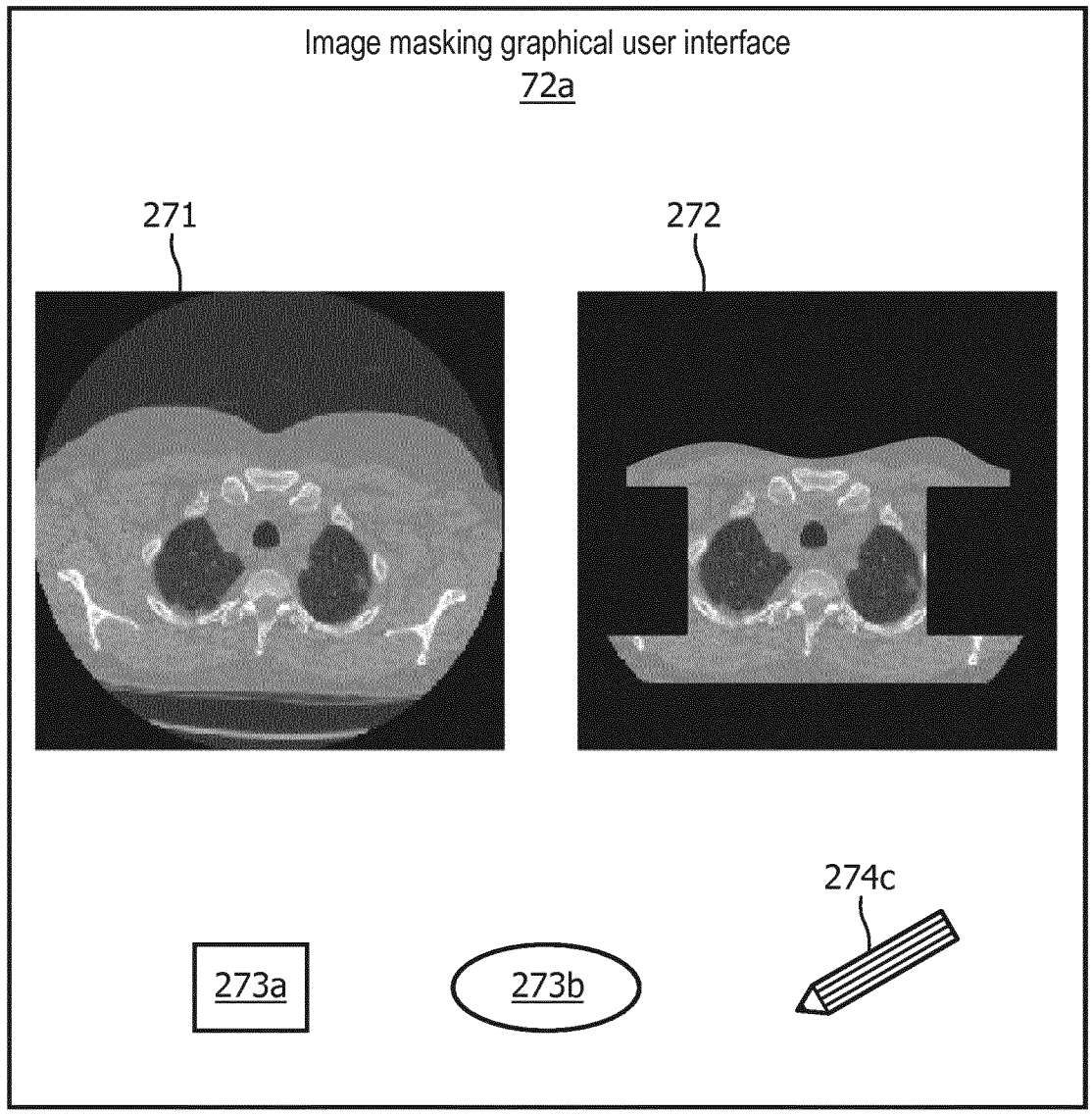
FIG. 10A illustrates an exemplary embodiment of an image masking graphical user interface (GUI) in accordance with the principles of the present disclosure.

FIG. 10A shows an embodiment 72a of an image masking GUI 72 providing for a clinician specification of image masking by data pre-processor 41 of AI engine 40 (FIG. 2A) to thereby see how AI engine 40 responds to a masking of one or more regions of a 2D medical planar image or a 3D medical volume image. If the clinician suspects the highlighted region of the 2D medical planar image or the 3D medical volume image is irrelevant, then the clinician may mask the irrelevant region and see the impact such masking has on prediction x or on a hypothesized prediction y. As shown in FIG. 7B, image masking GUI 72a of the present disclosure may concurrently display medical image 46a and 46b whereby a clinician may utilizes tool icons 273a, 273b and 274c to mask areas of medical image 272 while using medical image 271 as an original reference.

If GUI 70 ascertains during stage S174 that the input data is for data masking, then GUI 70 proceed to a stage S176 of flowchart 170 to communicate data masking data 34a to AI engine 40 whereby AI engine 40 executes S142-S146 of flowchart 140 (FIG. 2B) as previously described herein and medical imaging display engine 50 executes stages S154 (FIG. 2C) as previously described herein.

If GUI 70 ascertains during stage S178 that the input data is not for data masking, the GUI 70 proceeds to a stage S178 of flowchart 170 to ascertain if the input data is data revising data 34b received via data revising tab 73 whereby a clinician may test the influence of each input into the artificial intelligence engine 40 on feature assessment 31 of medical imaging 30 as visualized by salient image(s) 30. Examples of a data revision include, but are not limited to, (1) an enabling/disabling a medical imaging input or a combination of medical imaging inputs of the artificial intelligence engine, (2) an increasing/decreasing the pixel/voxel intensity value of medical imaging input or a combination of medical imaging inputs of the artificial intelligence engine, (3) an enabling/disabling an auxiliary information input or a combination of auxiliary information inputs of the artificial intelligence engine, or (4) an altering an auxiliary information input or a combination of auxiliary information inputs of the artificial intelligence engine.

Figure 10B:
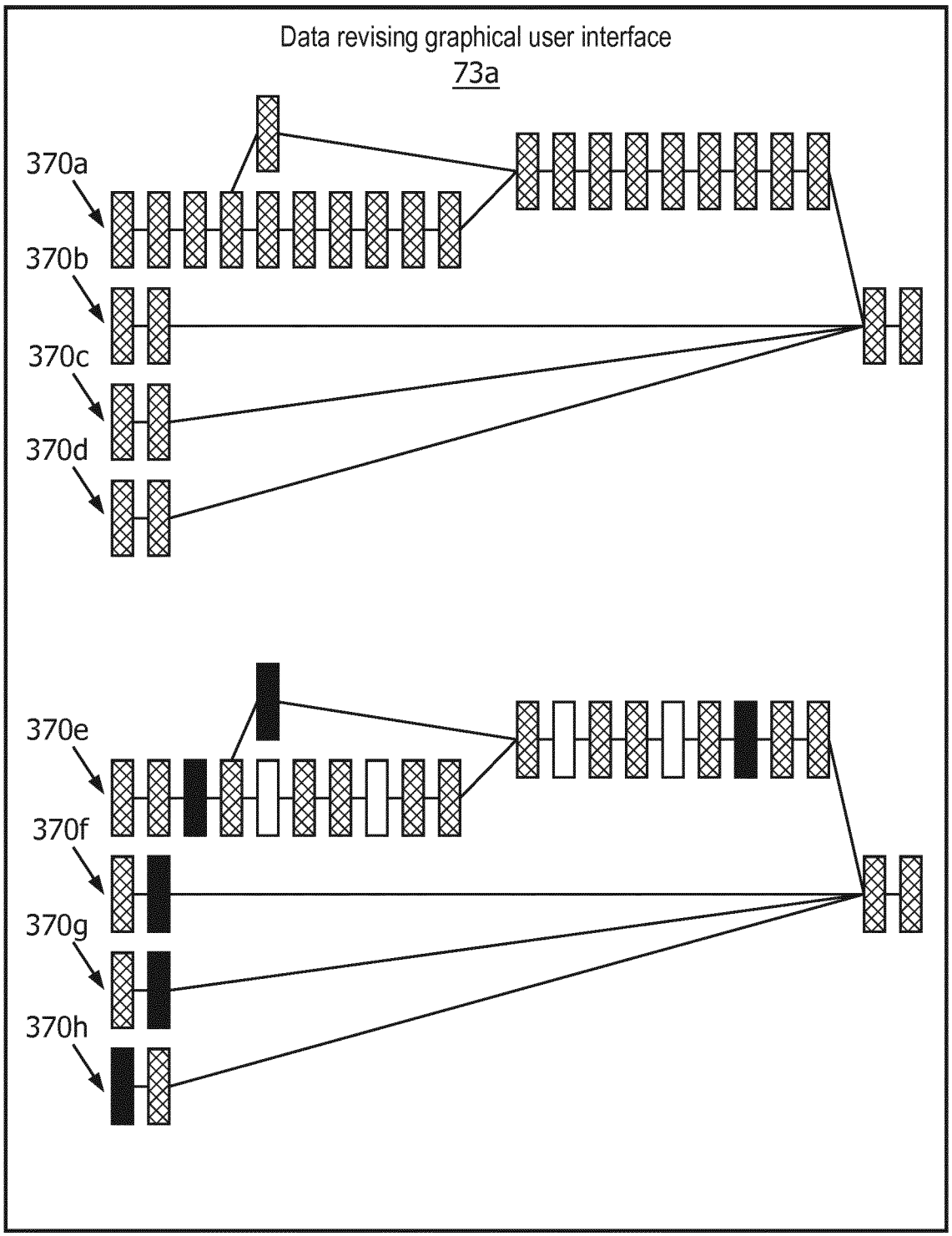
FIG. 10B illustrates an exemplary embodiment of a date revising graphical user interface (GUT) in accordance with the principles of the present disclosure.

FIG. 10B shows an embodiment 73a of data revising GUI 73 providing a clinician specification of the data input configuration of a AI engine 40 to test the influence of each input to the resulting feature assessment 31 of the 2D/3D medical imaging 30. In one embodiment, a data manipulation GUI of the present disclosure enables a clinician to switch on and off one or combination of image elements (e.g., pixels or voxels) as well as vary the input values via sliders, toggle buttons, etc. By observing a resulting salient visual images 30, the clinician may visually assess the influence of each input on the prediction accuracy and therefore either eliminate in the future all irrelevant information or understand the importance of each input. More particularly as shown in FIG. 10B, AI engine 40 may contain both main input image elements 370 (e.g., pixels or voxels) and several auxiliary information (e.g., a nodule radius 371, a nodule sphericity 372 and an output from another machine learning model 373). The main input may be either the 2D or 3D image. Auxiliary inputs may also include set of words present in the image annotation, patient age or medical history, output or combination of outputs from image processing or machine learning algorithms, as well as images from other modalities that are registered to the main input image. A data revising GUI 73a of the present disclosure provides for the revision of inputs 370-373, such as, for example, via revised inputs 370'-373' having revisions symbolized by blacked or whitened inputs.

If GUI 70 ascertains during stage S178 that the input data is for data revising, then GUI 70 proceed to a stage S180 of flowchart 170 to communicate data revising data 34a to AI engine 40 whereby AI engine 40 executes S142-S146 of flowchart 140 (FIG. 2B) as previously described herein and medical imaging display engine 50 executes stages S154 (FIG. 2C) as previously described herein.

If GUI 70 ascertains during stage S178 that the input data is not for data revising, the GUI 70 proceeds to a stage S182 of flowchart 170 to ascertain if the input data is feature relevancy threshold data 35a received via relevance threshold tab 74 whereby a clinician setting of a relevance level of the pixels of a planar medical image to the feature assessment 31 of the planar medical image or a clinician setting of a relevance level of the voxels of a volumetric medical image to the feature assessment 31 of the volumetric medical image. The insight is that not all pixels of a planar medical image or all voxels of a volumetric planar image are equally relevant to the feature assessment 31 and clinicians typically focus on feature(s) of the image they think are most suspicious. As such, the relevancy level of pixels of a planar medical image or voxels of a volumetric planar image may be set by a clinician to a value so that a feature of the image will be more distinctively highlighted within the salient image(s) 33 if this feature reaches that level of relevance.

Figure 10C:
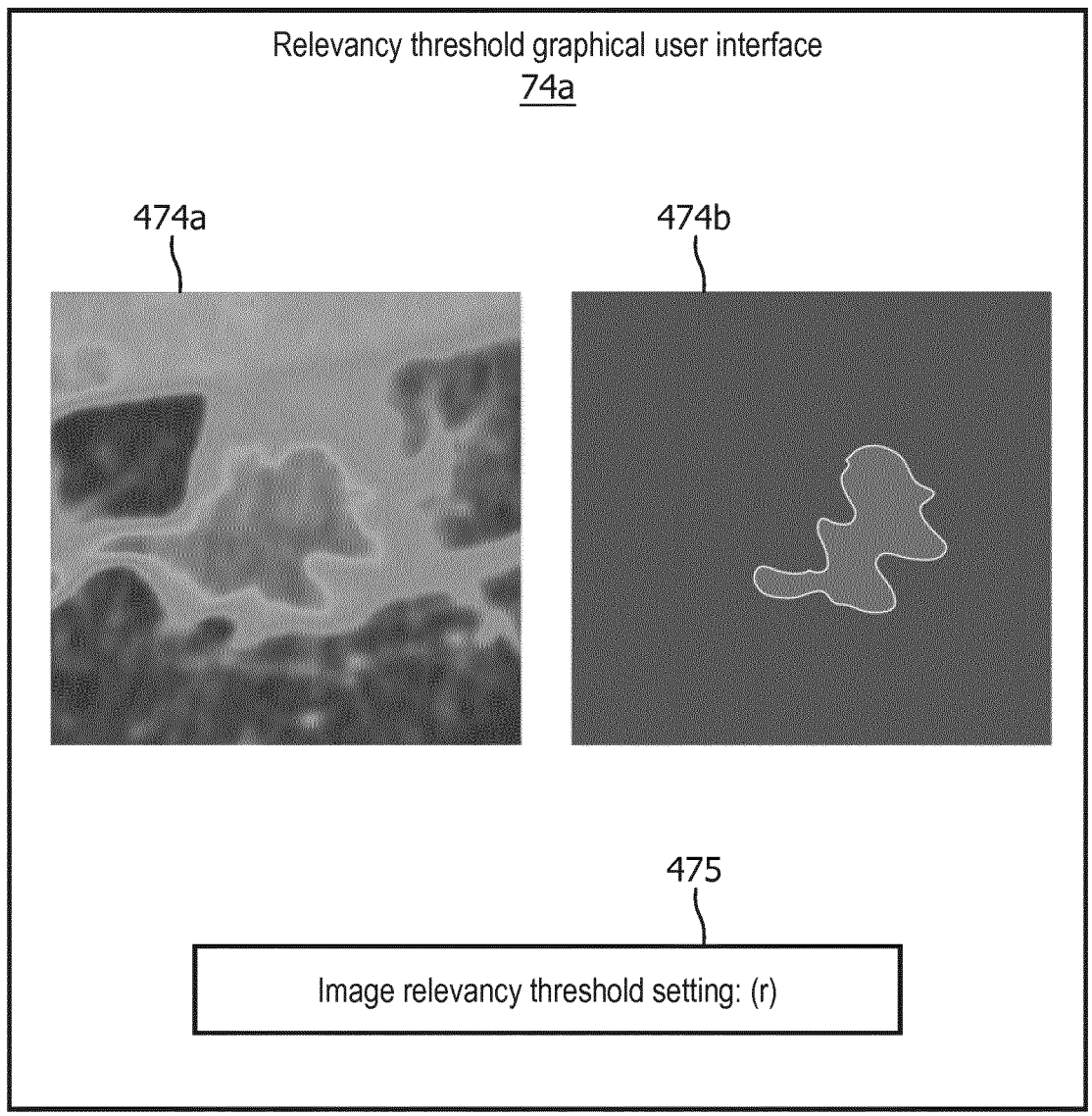
FIG. 10C illustrates an exemplary embodiment of relevancy threshold graphical user interface (GUI) in accordance with the principles of the present disclosure.

FIG. 10C shows an embodiment 74a of relevancy threshold GUI 74 providing for a clinician specification of a configuration of a AI engine 40 (FIG. 1) as to the relevancy levels of pixels of a 2D medical imaging of an anatomical region/organ to a particular risk prediction/status classification or the voxels of a 3D medical imaging to a particular risk prediction/status classification. The insight is that not all areas of a 2D medical planar image or of a 3D medical volume image are equally relevant to a specific diagnosis decision and clinicians typically focus on areas they think are most suspicious. In one embodiment, an image relevancy GUI of the present disclosure controls a display of a 2D reconstructed medical image or 3D medical volume image whereby the clinician may set the level of relevance of one or more regions to a value so that region(s) in the 2D medical planar image or in the 3D medical volume image will be highlighted if these region(s) reach that level of relevance. For example, as shown in FIG. 10C, image relevancy GUI 74a of the present disclosure may display a 2D heat map 44a (or alternatively a 3D heat map) from the feature assessment whereby a clinician may use an interface 475 to revise relevancy levels (r) of feature elements of AI engine 40 to control a display of a revised 2D heat map 44b (or alternatively a revised 3D heat map) focusing on areas deemed most relevant to the feature assessment. More particularly as related to FIGS. 4A and 4B, the clinician may exemplarily specify any intensity below 135.2 may be the same color (e.g., blue) and any intensity above 135.2 may be the same color (e.g., red) or the clinician may exemplarily specify any intensity below 67.6 may be the same color (e.g., blue) and all intensity above 135.2 will follow a linear change in color as shown.

If GUI 70 ascertains during stage S182 that the input data is for relevancy threshold specification, then GUI 70 proceed to a stage S184 of flowchart 170 to communicate relevancy threshold data 34a to AI engine 40 whereby AI engine 40 executes S144 and S146 of flowchart 140 (FIG. 2B) as previously described herein and medical imaging display engine 50 executes stages S154 (FIG. 2C) as previously described herein.

If GUI 70 ascertains during stage S182 that the input data is not for relevancy threshold specification, the GUI 70 proceeds to a stage S186 of flowchart 170 to ascertain if the input data is alternative feature assessment data 35b received via alternative assessment tab 75 whereby a clinician may hypothesize between different predictions or different classifications of the feature assessment 31 of medical imaging 30 (e.g., prediction/classification x and prediction/classification y), and if the artificial intelligence engine renders prediction/classification x of medical imaging 30 as visualized by salient image(s) 31 illustrative of prediction/classification x of medical imaging 30, then the clinician may select prediction/classification y via the GUI to see the features that are most relevant to prediction/classification y of medical imaging 30 as visualized by salient image(s) 31 illustrative of prediction/classification y of medical imaging 30.

Figure 10D:
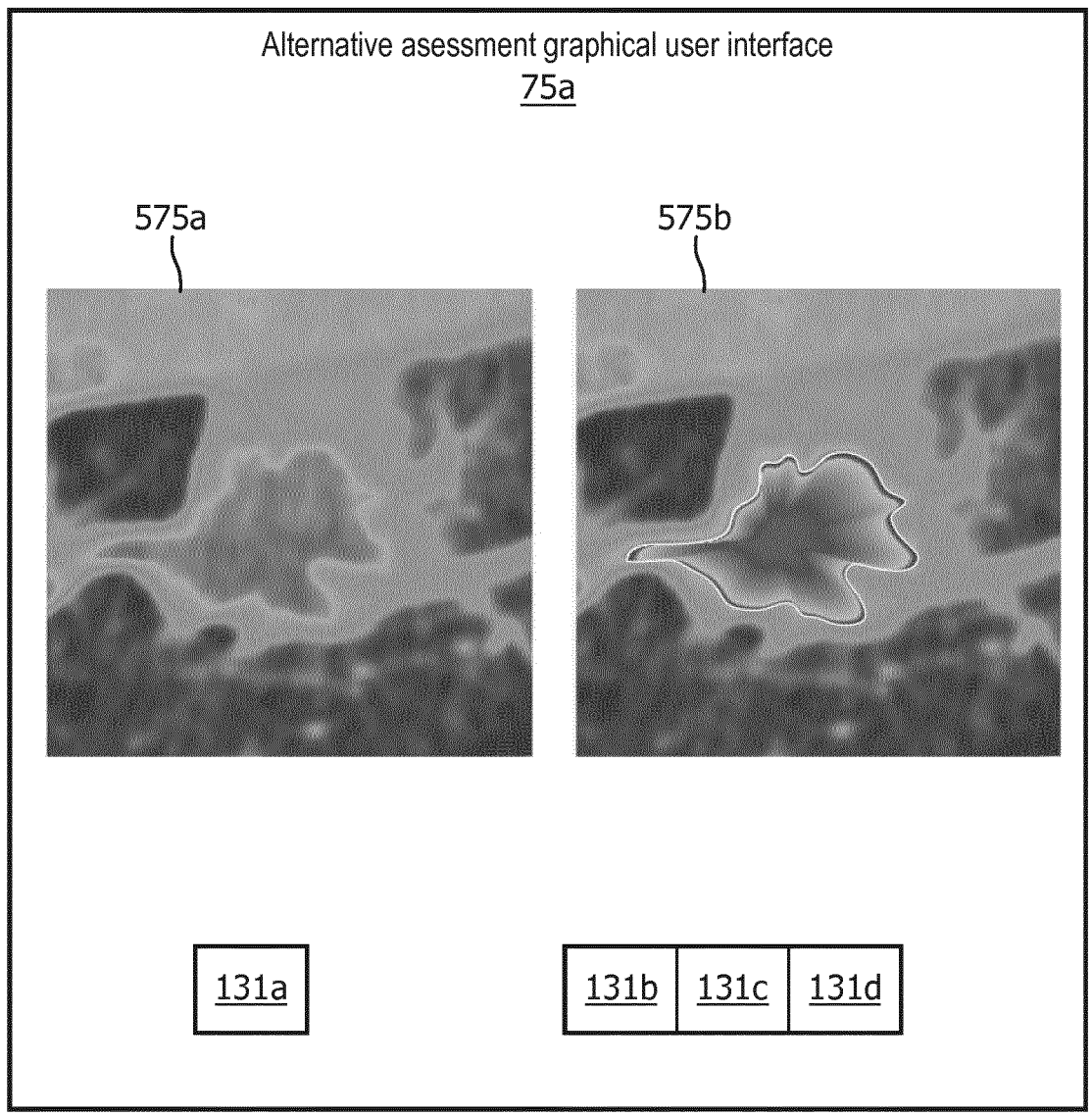
FIG. 10D illustrates an exemplary embodiment of an alternative assessment graphical user interface (GUI) in accordance with the principles of the present disclosure.

FIG. 10D shows an embodiment 74a of alternative assessment GUI 75 providing user selection of an alternative feature assessment whereby if AI engine 40 renders an initial feature assessment, then the clinician may see the areas that are most relevant to the alternative feature assessment. For example, as shown in FIG. 10D, alternative assessment GUI 75a displays a planar heat map 575a (or alternatively a 3D heat map) of the initial feature assessment 131a. Alternative assessment GUI 75 enables a clinician to select one of alternative feature assessments 131b-131d to display a revised 2D heat map 575b illustrative of the image features relevant to the selected alternative feature assessment. By further example, assessment outputs of a AI engine 40 (FIG. 1) may be based on a multi-categorical lesion classification of normal, glioblastoma, sarcoma and brain metastatic tumor. The initial feature assessment 131a may be sarcoma and 2D heat map 575b illustrates the sarcoma assessment whereby the clinician may select normal (131b), glioblastoma (131c) or brain metastatic tumor (131d) to thereby see the image features relevant to the selected alternative feature assessment.

If GUI 70 ascertains during stage S186 that the input data is for relevancy threshold specification, then GUI 70 proceed to a stage S188 of flowchart 170 to communicate relevancy threshold data 34a to AI engine 40 whereby AI engine 40 executes S144 and S146 of flowchart 140 (FIG. 2B) as previously described herein and medical imaging display engine 50 executes stages S154 (FIG. 2C) as previously described herein.

If GUI 70 ascertains during stage S186 that the input data is not for an alternative assessment specification, the GUI 70 returns to stage S172.

Figure 11:
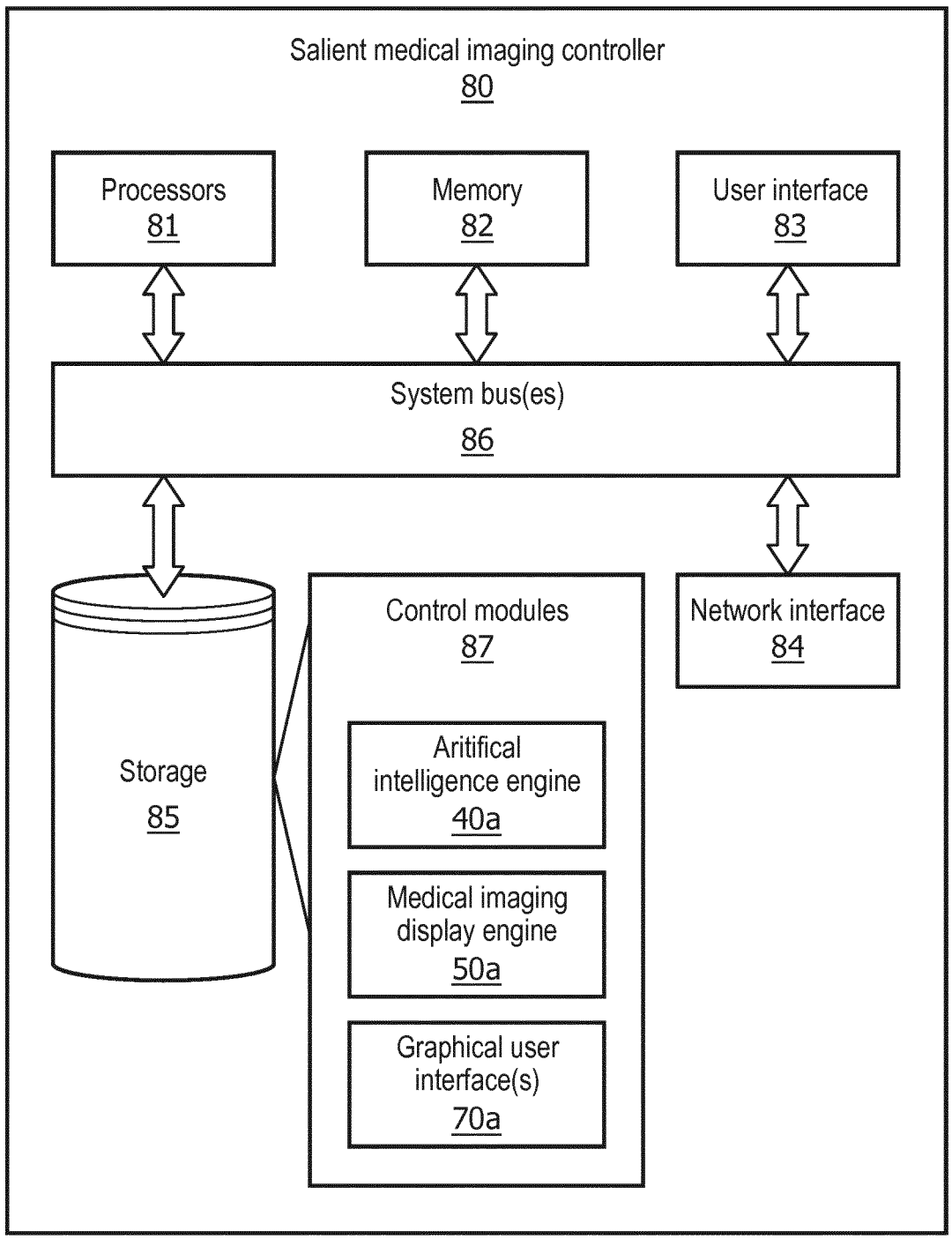
FIG. 11 illustrates an exemplary embodiment of a salient medical imaging controller in accordance with the principles of the present disclosure.
Figure 12A:
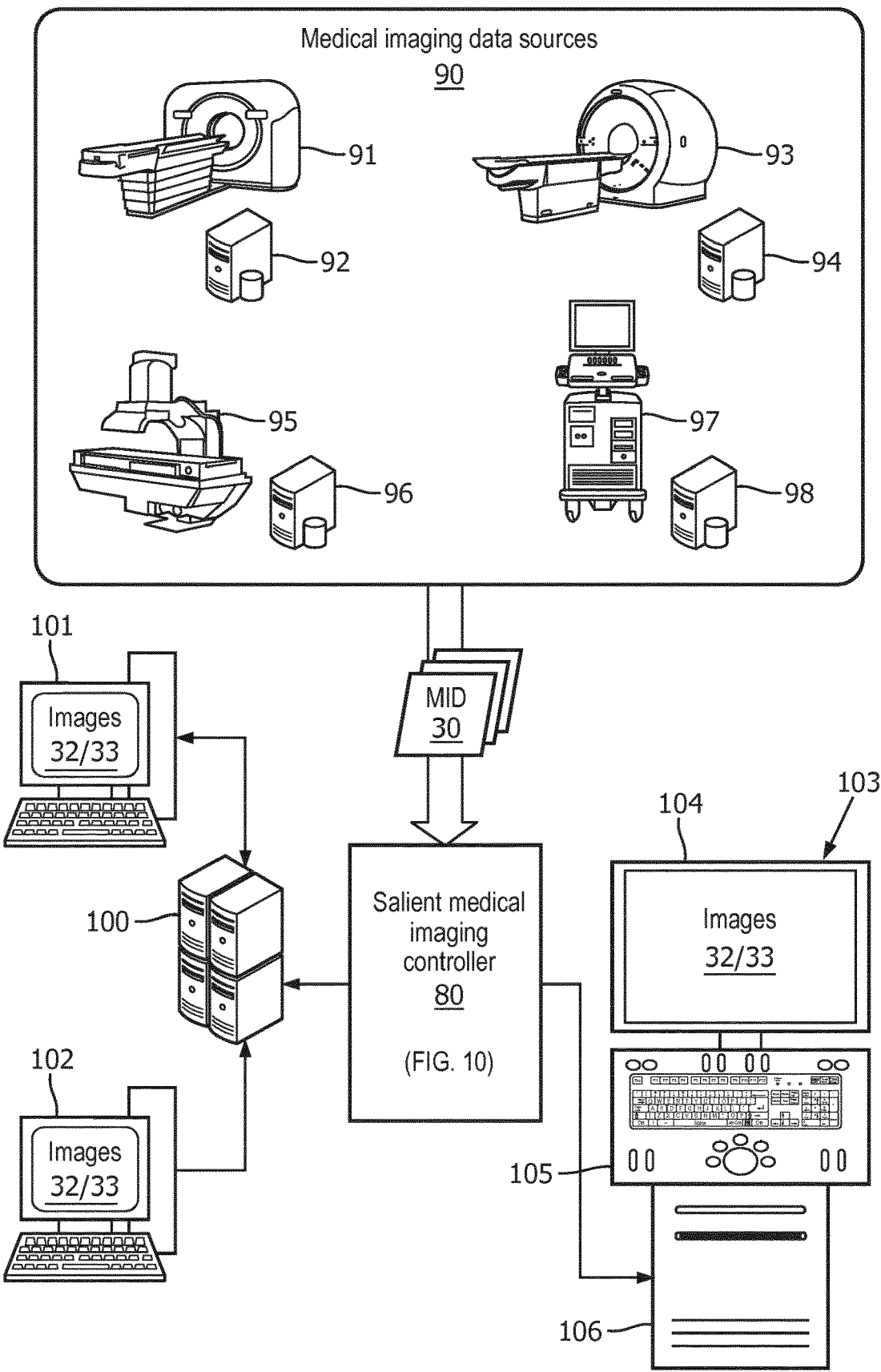
FIG. 12A illustrates a first exemplary embodiment of a salient medical imaging system in accordance with the principles of the present disclosure.
Figure 12B:
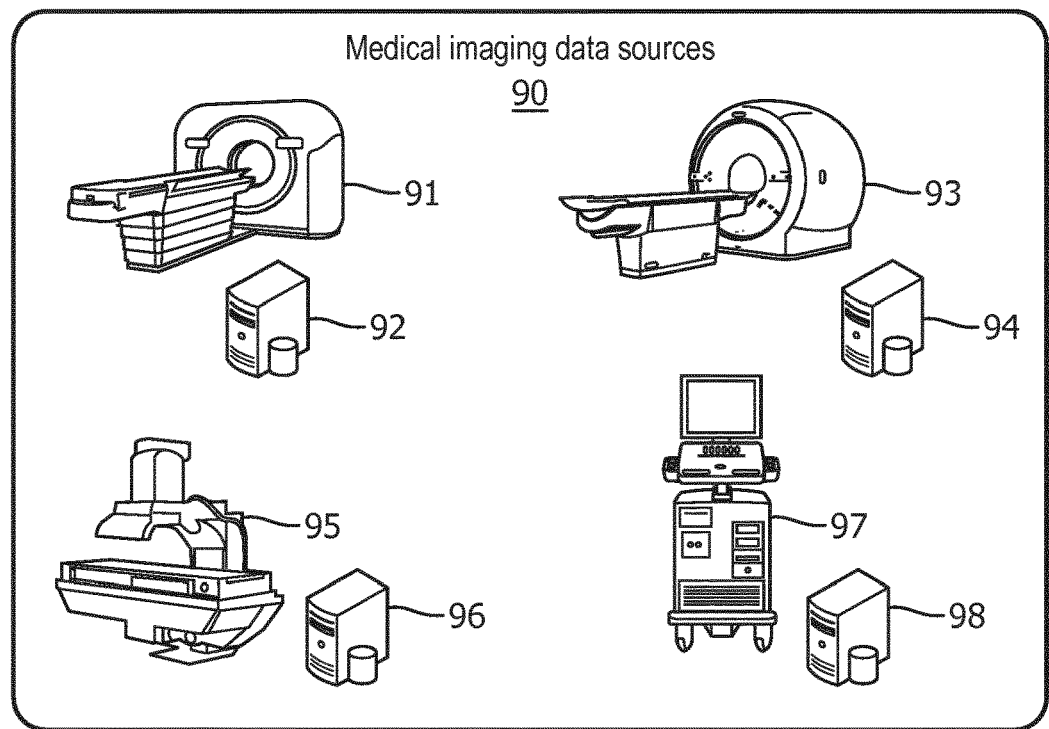
FIG. 12B illustrates a second exemplary embodiment of a salient medical imaging system in accordance with the principles of the present disclosure.
Figure 12B:
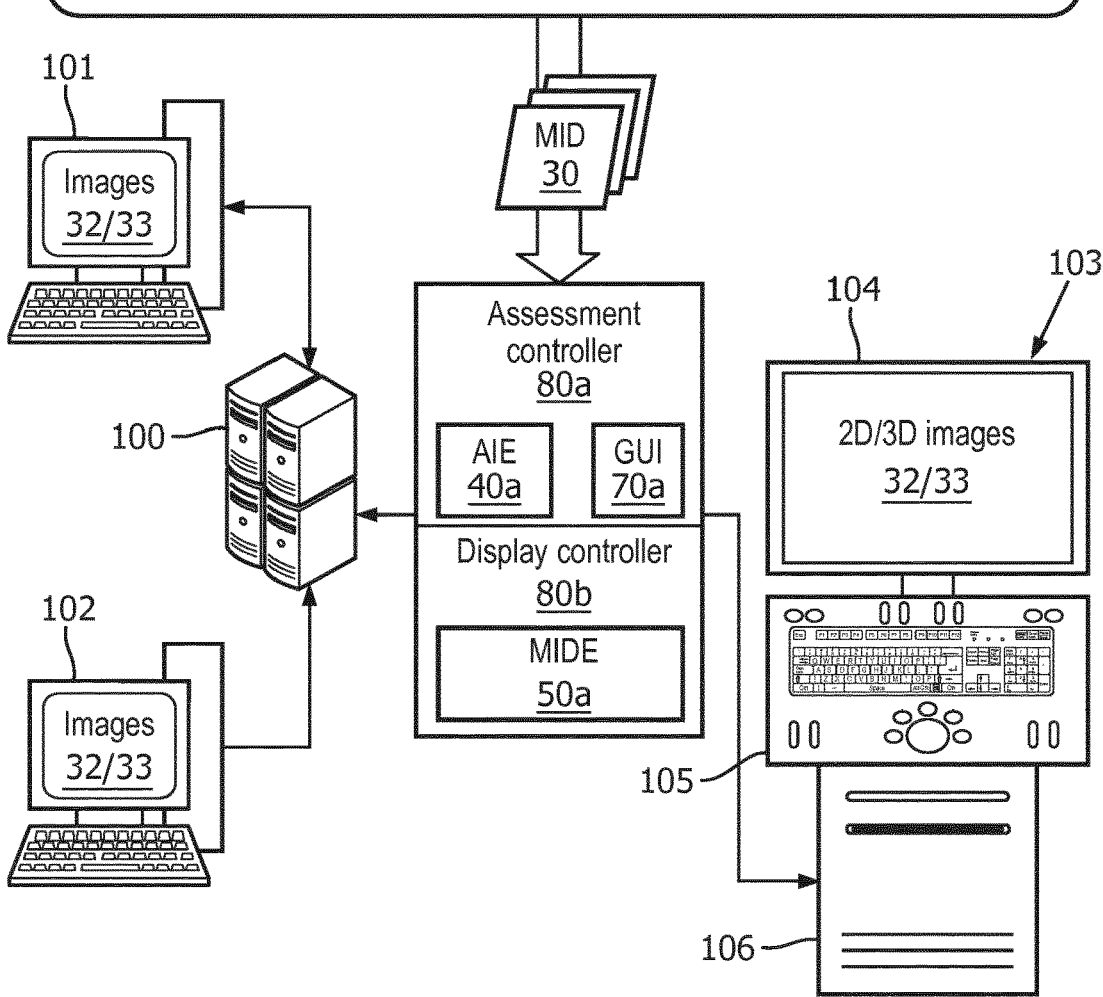

To further facilitate an understanding of the present disclosure, the following description of FIG. 11 teaches various embodiments of a salient medical imaging controller of the present disclosure and the following description of FIG. 12 teaches various embodiments of salient visualization system of the present disclosure. From the description of FIGS. 11 and 12, those having ordinary skill in the art of the present disclosure will appreciate how to apply the present disclosure for making and using numerous and various additional embodiments of salient medical imaging controller of the present disclosure.

In practice, a salient medical imaging controller of the present disclosure may be embodied as hardware/circuitry/software/firmware for implementation of a salient medical imaging method of the present disclosure as previously described herein. Further in practice, a salient medical imaging controller may be customized and installed in a server, workstation, etc. or programmed on a general purpose computer.

In one embodiment as shown in FIG. 11, a salient medical imaging controller 80 includes a processor 81, a memory 82, a user interface 83, a network interface 84, and a storage 85 interconnected via one or more system bus(es) 86. In practice, the actual organization of the components 81-85 of controller 80 may be more complex than illustrated.

The processor 81 may be any hardware device capable of executing instructions stored in memory or storage or otherwise processing data. As such, the processor 81 may include a microprocessor, field programmable gate array (FPGA), application-specific integrated circuit (ASIC), or other similar devices.

The memory 82 may include various memories such as, for example L1, L2, or L3 cache or system memory. As such, the memory 82 may include static random access memory (SRAM), dynamic RAM (DRAM), flash memory, read only memory (ROM), or other similar memory devices.

The user interface 83 may include one or more devices for enabling communication with a user such as an administrator. For example, the user interface 83 may include a display, a mouse, and a keyboard for receiving user commands. In some embodiments, the user interface 83 may include a command line interface or graphical user interface that may be presented to a remote terminal via the network interface 84.

The network interface 84 may include one or more devices for enabling communication with other hardware devices. For example, the network interface 84 may include a network interface card (NIC) configured to communicate according to the Ethernet protocol. Additionally, the network interface 84 may implement a TCP/IP stack for communication according to the TCP/IP protocols. Various alternative or additional hardware or configurations for the network interface will be apparent.

The storage 85 may include one or more machine-readable storage media such as read-only memory (ROM), random-access memory (RAM), magnetic disk storage media, optical storage media, flash-memory devices, or similar storage media. In various embodiments, the storage 85 may store instructions for execution by the processor 81 or data upon with the processor 81 may operate. For example, the storage 85 store a base operating system (not shown) for controlling various basic operations of the hardware.

More particular to the present disclosure, storage 85 may store control modules 87 in the form of a AI engine 40a as an embodiment of AI engine 40 (FIG. 2A), a medical image display engine 50a as an embodiment of medical image display engine 50 (FIG. 2A) and graphical user interface(s) 70a as an embodiment of AI engine 70 (FIG. 8A).

Referring to FIG. 12A, in practice, salient medical imaging controller 80 may be installed/programmed within an application server 100 accessible by a plurality of clients (e.g., a client 101 and a client 102 as shown) and/or is installed/programmed within a workstation 103 employing a monitor 104, a keyboard 105 and a computer 106.

In operation, salient medical imaging controller 80 inputs medical imaging data 30, planar or volumetric, from medical imaging data sources 80 during a training phase and a phase. Medical imaging data sources 90 may include any number and types of medical imaging machines (e.g., a MRI machine 91, a CT machine 93, an X-ray machine 95 and an ultrasound machine 97 as shown) and may further includes database management/file servers (e.g., MRI database management server 92, CT server 94, X-ray database management server 96 and ultrasound database manager server 97 as shown). In practice, application server 100 or workstation 103, whichever is applicable, may be directly or networked connected to a medical imaging data source 90 to thereby input medical imaging data 30 for salient medical imaging controller 80. Alternatively, a medical imaging data source 90 and application server 100 or workstation 103, whichever is applicable, may be directly integrated whereby the salient medical imaging controller 80 has direct access to medical imaging data 30.

FIG. 12B illustrates an alternative embodiment of salient medical imaging controller 80 segregated into an assessment controller 80a for implementing AI engine 40a and GUIs 70a, and a display controller 80b for medical imaging display engine 50a. For this embodiment, assessment controller 80a and display controller 80b may be installed/programmed within application server 100 or workstation 103, or alternatively may be distributively installed/programmed between application server and workstation 103.

Referring to FIGS. 1-12, those having ordinary skill in the art will appreciate the many benefits of the present disclosure including, but not limited to, a visualization by a clinician of a feature assessment by machine learning model (s) of a medical imaging of a body, human or animal, that facilitates a clear and concise understanding by the clinician of the feature assessment.

Furthermore, it will be apparent that various information described as stored in the storage may be additionally or alternatively stored in the memory. In this respect, the memory may also be considered to constitute a "storage device" and the storage may be considered a "memory." Various other arrangements will be apparent. Further, the memory and storage may both be considered to be "non-transitory machine-readable media." As used herein, the term "non-transitory" will be understood to exclude transitory signals but to include all forms of storage, including both volatile and non-volatile memories.

While the device is shown as including one of each described component, the various components may be duplicated in various embodiments. For example, the processor may include multiple microprocessors that are configured to independently execute the methods described in the present disclosure or are configured to perform steps or subroutines of the methods described in the present disclosure such that the multiple processors cooperate to achieve the functionality described in the present disclosure. Further, where the device is implemented in a cloud computing system, the various hardware components may belong to separate physical systems. For example, the processor may include a first processor in a first server and a second processor in a second server.

It should be apparent from the foregoing description that various example embodiments of the invention may be implemented in hardware or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A medical image saliency controller, comprising:
a memory storing an artificial intelligence engine and a graphical user interface, wherein the artificial intelligence engine includes at least one machine learning model; and
a processor in communication with the memory, the processor being configured to:
apply the at least one machine learning model to a medical image data representative of at least one feature of a volumetric medical image to render a feature assessment of the volumetric medical image; and
control a display of the graphical user interface providing a user interaction with the artificial intelligence engine to manipulate a salient visualization of the feature assessment of the volumetric medical image by the at least one machine learning model;
wherein generating the salient visualization comprises reslicing a planar salient image from the assessed volumetric medical image based on a relevancy level of each feature of the assessed volumetric medical image to the feature assessment.

2. The medical image saliency controller of claim 1, wherein the control of the display of the graphical user interface providing the user interaction with the artificial intelligence engine to manipulate the salient visualization of the feature assessment of the volumetric medical image includes:
the processor being further configured to control the display of the graphical user interface providing a user specification of a relevancy threshold for each feature of the volumetric medical image to the salient visualization of the feature assessment of the volumetric medical image.

3. The medical image saliency controller of claim 1, wherein the control of the display of the graphical user interface providing the user interaction with the artificial intelligence engine to manipulate the salient visualization of the feature assessment of the volumetric medical image includes:
the processor being further configured to control the display of the graphical user interface providing a user specification of an alternative feature assessment of the volumetric medical image by the at least one machine learning model.

4. The medical image saliency controller of claim 1, wherein the control of the display of the graphical user interface providing the user interaction with the artificial intelligence engine to manipulate the salient visualization of the feature assessment of the volumetric medical image includes:
the processor being further configured to control the display of the graphical user interface providing a user specification of a masking of at least one of the features of the volumetric medical image.

5. The medical image saliency controller of claim 1, wherein the control of the display of the graphical user interface providing the user interaction with the artificial intelligence engine to manipulate the salient visualization of the feature assessment of the volumetric medical image includes:
the processor being further configured to control the display of the graphical user interface providing a user specification of a revision of at least one of the features of the volumetric medical image.

6. The medical image saliency controller of claim 1,
wherein the memory further stores an image display engine; and
wherein the processor is further configured to:
control a display of a salient image generated by the image display engine, the salient image being illustrative of the salient visualization of the feature assessment of the volumetric medical image.

7. The medical image saliency controller of claim 6, wherein the control of the display of the graphical user interface providing the user interaction with the artificial intelligence engine to manipulate the salient visualization of the feature assessment of the volumetric medical image includes:
the processor being further configured to control the display of the graphical user interface including at least one of the salient image and the volumetric medical image.

8. The medical image saliency controller of claim 6, wherein the salient visualization of the feature assessment of the medical image includes at least one of a heat map, a feature segmentation and an activation diagram.

9. A non-transitory machine-readable storage medium encoded with instructions for execution by at least one processor, the non-transitory machine-readable storage medium comprising instructions to:
apply an artificial intelligence engine including at least one machine learning model to a medical image data representative of at least one feature of a volumetric medical image to render a feature assessment of the volumetric medical image; and
control a display of a graphical user interface providing a user interaction with the artificial intelligence engine to manipulate a salient visualization of the feature assessment of the volumetric medical image by the at least one machine learning model
wherein generating the salient visualization comprises reslicing a planar salient image from the assessed volumetric medical image based on a relevancy level of each feature of the assessed volumetric medical image to the feature assessment.

10. The non-transitory machine-readable storage medium of claim 9, wherein the instructions to control of the display of the graphical user interface providing the user interaction with the artificial intelligence engine to manipulate the salient visualization of the feature assessment of the volumetric medical image include:
instructions to control of the display of the graphical user interface providing a user specification of a relevancy threshold for each feature of the volumetric medical image to the salient visualization of the feature assessment of the volumetric medical image.

11. The non-transitory machine-readable storage medium of claim 9, wherein the instructions to control of the display of the graphical user interface providing the user interaction with the artificial intelligence engine to manipulate the salient visualization of the feature assessment of the volumetric medical image include:
instructions to control the display of the graphical user interface providing a user specification of an alternative feature assessment of the volumetric medical image by the at least one machine learning model.

12. The non-transitory machine-readable storage medium of claim 9, wherein the instructions to control of the display of the graphical user interface providing the user interaction with the artificial intelligence engine to manipulate the salient visualization of the feature assessment of the volumetric medical image include:
instructions to control the display of the graphical user interface providing a user specification of a masking of at least one of the features of the volumetric medical image.

13. The non-transitory machine-readable storage medium of claim 9, wherein the instructions to control of the display of the graphical user interface providing the user interaction with the artificial intelligence engine to manipulate the salient visualization of the feature assessment of the medical volumetric image include:
instructions to control the display of the graphical user interface providing a user specification of a revision of at least one of the features of the volumetric medical image.

14. The non-transitory machine-readable storage medium of claim 9, wherein the non-transitory machine-readable storage medium further comprises instructions to:
control a display of a salient image generated by an image display engine, the salient image being illustrative of the salient visualization of the feature assessment of the volumetric medical image.

15. The non-transitory machine-readable storage medium of claim 14, wherein the instructions to control of the display of the graphical user interface providing the user interaction with the artificial intelligence engine to manipulate the salient visualization of the feature assessment of the medical image include:
instructions to control the display of the graphical user interface including at least one of the salient image and the volumetric medical image.

16. A medical image saliency method, comprising:
applying an artificial intelligence engine including at least one machine learning model to a medical image data representative of at least one feature of a volumetric medical image to render a feature assessment of the medical image; and
controlling a display of the graphical user interface providing a user interaction with the artificial intelligence engine to manipulate a salient visualization of the feature assessment of the volumetric medical image by the at least one machine learning model
wherein generating the salient visualization comprises reslicing a planar salient image from the assessed volumetric medical image based on a relevancy level of each feature of the assessed volumetric medical image to the feature assessment.

17. The medical image saliency method of claim 16, wherein the controlling of the display of the graphical user interface providing the user interaction with the artificial intelligence engine to manipulate the salient visualization of the feature assessment of the volumetric medical image includes:
controlling the display of the graphical user interface providing a user specification of a relevancy threshold for each feature of the medical image to the salient visualization of the feature assessment of the volumetric medical image.

18. The medical imaging saliency method of claim 16, wherein the controlling of the display of the graphical user interface providing the user interaction with the artificial intelligence engine to manipulate the salient visualization of the feature assessment of the medical image includes:
controlling the display of the graphical user interface providing a user specification of an alternative feature assessment of the medical image by the at least one least one machine learning model.

19. The medical image saliency method of claim 16, wherein the controlling of the display of the graphical user interface providing the user interaction with the artificial intelligence engine to manipulate the salient visualization of the feature assessment of the volumetric medical image includes:
   controlling the display of the graphical user interface providing a user specification of a masking of at least one of the features of the volumetric medical image.

20. The medical image saliency method of claim 16, wherein the controlling of the display of the graphical user interface providing the user interaction with the artificial intelligence engine to manipulate the salient visualization of the feature assessment of the volumetric medical image includes:
   controlling the display of the graphical user interface providing a user specification of a revision of at least one of the features of the volumetric medical image.

* * * * *